US011268381B2

(12) United States Patent
Amanullah et al.

(10) Patent No.: US 11,268,381 B2
(45) Date of Patent: Mar. 8, 2022

(54) ADDITIVE MANUFACTURING OF A VUGULAR LOSS ZONE SIMULATING TEST DEVICE

(71) Applicant: SAUDI ARABIAN OIL COMPANY, Dhahran (SA)

(72) Inventors: Md Amanullah, Dhahran (SA); Abrar Alshaikh, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 0 days.

(21) Appl. No.: 16/867,258

(22) Filed: May 5, 2020

(65) Prior Publication Data

US 2020/0370431 A1  Nov. 26, 2020

Related U.S. Application Data

(63) Continuation-in-part of application No. 15/879,783, filed on Jan. 25, 2018, now Pat. No. 11,111,742.
(Continued)

(51) Int. Cl.
*E21B 49/08* (2006.01)
*G01N 33/28* (2006.01)
*B33Y 80/00* (2015.01)

(52) U.S. Cl.
CPC ....... *E21B 49/087* (2013.01); *G01N 33/2823* (2013.01); *B33Y 80/00* (2014.12)

(58) Field of Classification Search
CPC ................................................ G01N 33/2823
See application file for complete search history.

(56) References Cited

U.S. PATENT DOCUMENTS 2,646,678 A * 7/1953 Standing ............... B01D 29/111
  210/455
5,161,407 A  11/1992 Ankeny et al.
(Continued)

FOREIGN PATENT DOCUMENTS

EP  2875935 A1  5/2015
WO  2009029451 A1  3/2009
(Continued)

OTHER PUBLICATIONS

Whitfill, Donald L. and Matthew Miller, "Developing and Testing Lost Circulation Materials", AADE-08-DF-HO-24, AADE American Association of Drilling Engineers, Apr. 2008 (11 pages).
(Continued)

*Primary Examiner* — John Fitzgerald
(74) *Attorney, Agent, or Firm* — Osha Bergman Watanabe & Burton LLP

(57) ABSTRACT

A loss circulation material (LCM) testing apparatus includes an LCM testing cell. The LCM testing fluid is a slurry of LCM material and a wellbore drilling fluid. A fluid flow pathway within the LCM testing cell is defined between an inlet and an outlet. The LCM testing cell includes a disk member that is removable positioned in the fluid flow pathway between the inlet and the outlet of the LCM testing cell. The disk member includes a disk base and a plurality of downstream-directed extensions, which combined define a plurality of flow openings. A method of evaluating a loss circulation material (LCM) includes introducing a LCM testing fluid into the LCM testing cell and detecting an amount of LCM testing fluid traversing the LCM test cell.

24 Claims, 9 Drawing Sheets

Related U.S. Application Data

(60) Provisional application No. 62/472,353, filed on Mar. 16, 2017.

(56) References Cited

U.S. PATENT DOCUMENTS

| | | | |
|---|---|---|---|
| 6,055,850 A | 5/2000 | Turner et al. | |
| 8,573,048 B2* | 11/2013 | Slater | E21B 21/01 |
| | | | 73/152.18 |
| 8,863,567 B2* | 10/2014 | Jappy | E21B 21/003 |
| | | | 73/61.64 |
| 9,285,355 B2* | 3/2016 | Murphy | E21B 49/008 |
| 9,388,333 B2* | 7/2016 | Savari | C09K 8/426 |
| 9,587,490 B2* | 3/2017 | Kaarigstad | E21B 49/10 |
| 9,714,565 B2* | 7/2017 | Blue | G01N 33/2823 |
| 9,887,356 B2 | 2/2018 | McAlpine et al. | |
| 10,209,169 B2* | 2/2019 | Jamison | G01N 9/00 |
| 10,466,153 B2* | 11/2019 | Gupta | G01N 33/24 |
| 2008/0236891 A1* | 10/2008 | Huynh | G01N 15/08 |
| | | | 175/48 |
| 2010/0032031 A1* | 2/2010 | Neal | E21B 21/02 |
| | | | 137/565.01 |
| 2010/0139387 A1* | 6/2010 | Jamison | E21B 21/003 |
| | | | 73/152.25 |
| 2011/0290012 A1 | 12/2011 | Jappy et al. | |
| 2013/0192358 A1 | 8/2013 | Murphy et al. | |
| 2013/0218545 A1* | 8/2013 | Murphy | E21B 43/26 |
| | | | 703/10 |
| 2013/0298662 A1 | 11/2013 | Jamison et al. | |
| 2014/0102188 A1 | 4/2014 | Murphy et al. | |
| 2014/0182369 A1 | 7/2014 | Blue et al. | |
| 2014/0216149 A1 | 8/2014 | Zhou et al. | |
| 2016/0033382 A1* | 2/2016 | Jamison | G01N 11/04 |
| | | | 73/152.18 |
| 2016/0061701 A1 | 3/2016 | Amanullah et al. | |
| 2016/0130939 A1 | 5/2016 | Murphy et al. | |
| 2016/0131165 A1 | 5/2016 | Collins | |
| 2018/0266197 A1 | 9/2018 | Amanullah et al. | |
| 2019/0265150 A1 | 8/2019 | Everhard et al. | |
| 2020/0110014 A1* | 4/2020 | Amanullah | G01N 33/2823 |
| 2020/0110015 A1* | 4/2020 | Amanullah | G01N 15/0826 |
| 2021/0254450 A1* | 8/2021 | Hitchcock | E21B 47/09 |

FOREIGN PATENT DOCUMENTS

| | | |
|---|---|---|
| WO | 201064009 A1 | 6/2010 |
| WO | 2013126287 A1 | 8/2013 |
| WO | 2018005575 A1 | 1/2018 |

OTHER PUBLICATIONS

Miller, Matthew L. et al., "Laboratory Apparatus Improves Simulation of Lost Circulation Conditions", AADE-13-FTCE-09, AADE American Association of Drilling Engineers, Feb. 2013 (8 pages).

Smith, J.R. and F.B. Growcock, "Wellbore Strengthening While Drilling Above and Below Salt in the Gulf of Mexico", AADE-08-DF-HO-21, AADE American Association of Drilling Engineers, Apr. 2008 (6 pages).

"Permeability Plugging Apparatus Instruction Manual", Manual No. 204249, Revision E, Fann Instrument Company, May 2018 (60 pages).

Hettema, M. et al., "Development of an Innovative High-Pressure Testing Device for the Evaluation of Drilling Fluid Systems and Drilling Fluid Additives with Fractured Permeable Zones", Paper N. 041/dlg2, Offshore Mediterranena Conference and Exhibition, May 2007 (14 pages).

International Search Report issued in corresponding International Application No. PCT/US2020/046084, dated Nov. 9, 2020 (4 pages).

Written Opinion issued in corresponding International Application No. PCT/US2020/046084, dated Nov. 9, 2020 (7 pages).

International Search Report issued in related International Application No. PCT/US2018/022229, dated Jul. 6, 2018 (4 pages).

Written Opinion issued in related International Application No. PCT/US2018/022229, dated Jul. 6, 2018 (6 pages).

International Search Report issued in related International Application No. PCT/US2019/054408, dated Feb. 21, 2020 (4 pages).

Written Opinion issued in related International Application No. PCT/US2019/054408, dated Feb. 21, 2020 (9 pages).

\* cited by examiner

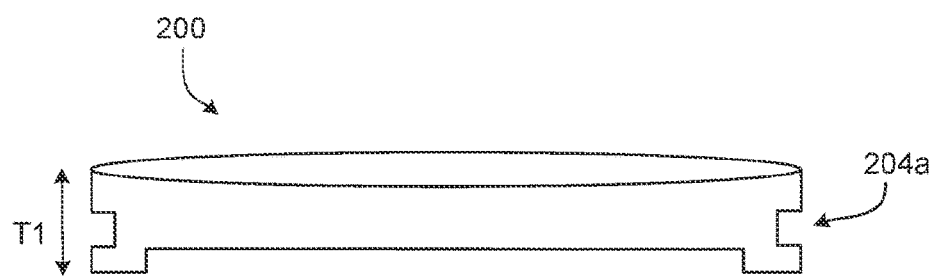
FIG. 2A
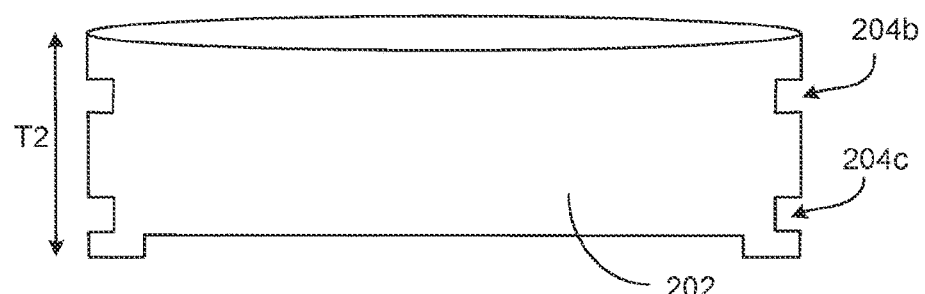
FIG. 2B
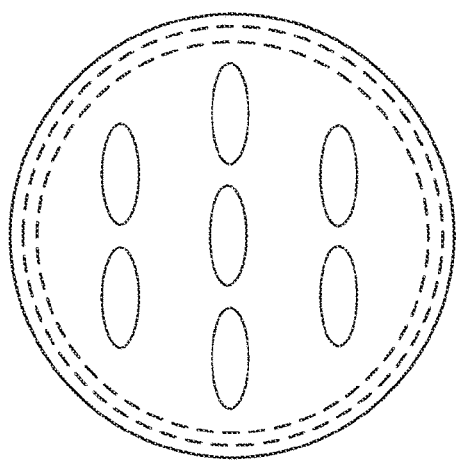 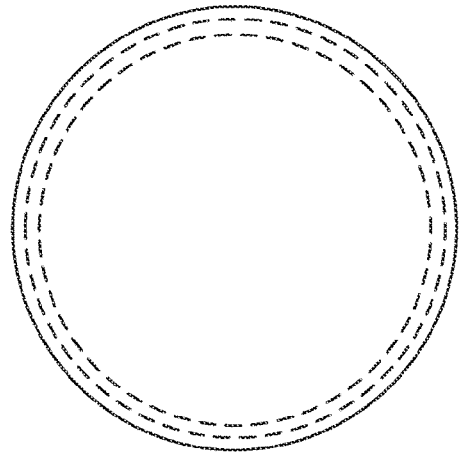
FIG. 2C          FIG. 2D

ADDITIVE MANUFACTURING OF A VUGULAR LOSS ZONE SIMULATING TEST DEVICE

CROSS-REFERENCE TO RELATED APPLICATION

This application is a continuation-in-part and claims the benefit of priority to U.S. patent application Ser. No. 15/879,783, filed Jan. 25, 2018, which claims the benefit of priority to U.S. Provisional Patent Application No. 62/472,353, filed Mar. 16, 2017, the contents of which are hereby incorporated by reference.

BACKGROUND

Technical Field

The disclosure relates generally to testing apparatus, for example, apparatus to test fluid flow into the formation of a wellbore.

Background

In wellbore drilling, a drilling fluid (or drilling mud) is circulated from a surface of the wellbore to downhole through the drill string. The fluid exits through ports (or jets) in the drill bit, picking up cuttings and carrying the cuttings up an annulus formed between an inner wall of the wellbore and an outer wall of the drill string. The fluid and the cuttings flow through the annulus to the surface, where the cuttings are separated from the fluid. The fluid can be treated with chemicals and then pumped into the wellbore through the drill string to repeat the process.

Lost circulation is a situation in which the flow of the drilling fluid up the annulus toward the surface is reduced or is totally absent. For example, lost circulation results because a portion of the subterranean zone encountered while drilling has a permeability, openings, flow channels, fractures, vugs and/or caves that causes all or a portion of the drilling fluid to be lost into these loss zones. Lost circulation can be countered by introducing loss circulation material (LCM) into the wellbore. The LCM reduces the permeability or fluid flow capability totally or partially of the portion of the subterranean zone minimizing or preventing loss of the drilling fluid into the portion.

SUMMARY

This specification describes technologies relating to LCM performance evaluation. This specification also describes a test apparatus to test and evaluate the performance of LCM.

Certain aspects of the subject matter described here can be implemented as a LCM testing apparatus. The apparatus includes a drilling fluid reservoir that can carry a wellbore drilling fluid. The apparatus includes a LCM reservoir that can carry a LCM. The apparatus includes a spacer fluid reservoir that can carry a spacer fluid. The apparatus includes a LCM test cell that includes various disk members that includes multiple openings of various sizes to simulate loss zone of various nature such as seepage, moderate and severe. The disk member represents a loss circulation zone in a subterranean zone in which a wellbore is drilled using the wellbore drilling fluid. The LCM test cell is fluidically connected to the drilling fluid reservoir, the LCM reservoir and the spacer fluid reservoir. The LCM test cell is configured to fluidically receive a quantity of LCM from the LCM reservoir and to evaluate an ability of the LCM to stop or decrease loss circulation through the loss circulation zone.

This, and other aspects, can include one or more of the following features. The apparatus can include a fluid transfer network, which can include four elongate tubular members. A first elongate tubular member can be fluidically coupled to the LCM test cell. A second elongate tubular member can be fluidically coupled to the drilling fluid reservoir and to the first elongate tubular member. A third elongate tubular member can be fluidically coupled to the drilling fluid reservoir and to the first elongate tubular member. A fourth elongate tubular member can be fluidically coupled to the spacer fluid reservoir and to the first elongate tubular member. The fluid transfer network can flow at least one of the wellbore drilling fluid, the LCM or the spacer fluid to the LCM test cell.

With or without any of the other aspects, the LCM test cell can be configured to evaluate a sealing efficiency of the LCM. The sealing efficiency is an ability of the LCM to prevent flow of wellbore drilling fluid through the plurality of openings in the disk member. The spacer fluid is incorporated in some cases to prevent the contamination of wellbore drilling fluid due to the mixing effect of LCM pill or loss control slurry with the drilling mud.

With or without any of the other aspects, each of the drilling fluid reservoir, the LCM reservoir, the spacer fluid reservoir and the LCM test cell can include a respective nitrogen pressure inlet configured to receive nitrogen and to transfer the received nitrogen to the LCM test cell to apply a pressure on a mixture of the wellbore drilling fluid and the spacer fluid including the quantity of the LCM to evaluate the ability of the LCM to decrease loss circulation through the simulated loss circulation zone.

With or without any of the other aspects, the apparatus can include a valve network, which can include four valves. A first valve can be in a flow path through the first elongate tubular member. A second valve can be in a flow path through the second elongate tubular member. A third valve can be in a flow path through the third elongate tubular member. A fourth valve can be in a flow path through the fourth elongate tubular member. The valve network can selectively flow at least one of the wellbore drilling fluid, the LCM or the spacer fluid to the LCM test cell.

With or without any of the other aspects, the apparatus can include a first base member supporting the drilling fluid reservoir, the LCM reservoir and the spacer fluid reservoir, and a second base member supporting the LCM test cell. The second base member can be positioned vertically lower than the first base member relative to a floor on which the first base member and the second base member are positioned, the floor being below the first base member and the second base member.

With or without any of the other aspects, the LCM test cell can include an inlet fluidically connected to the first elongate tubular member and an outlet. A LCM test cell region between the inlet and the outlet can define a fluid flow path. The disk member can be positioned within the flow path such that fluid flowed from the inlet to the outlet at least partially flows through the disk member.

With or without any of the other aspects, the LCM test cell can be pressurized up to 2000 pounds per square inch (psi).

With or without any of the other aspects, each of the drilling fluid reservoir, the spacer fluid reservoir and the LCM reservoir can be pressurized up to 500 psi.

With or without any of the other aspects, the disk member including the multiple openings can be a first disk member that includes multiple openings of various sizes, each of which is substantially up to 40 millimeter (mm) in size.

With or without any of the other aspects, the apparatus can include multiple disk members, each including multiple openings. A second of the multiple disk members can include openings ranging between substantially 5 mm and up to 40 mm in size.

Certain aspects of the subject matter described here can be implemented as a method of evaluating a LCM. Wellbore drilling fluid is stored in a drilling fluid reservoir. LCM is stored in a LCM reservoir. Spacer fluid is stored in a spacer fluid reservoir. The LCM test material is flowed to a LCM test cell fluidically coupled to the drilling fluid reservoir, the LCM reservoir and the spacer fluid reservoir. The LCM test material includes a quantity of LCM from the LCM reservoir. The LCM test material is pressurized to flow through a disk member including multiple openings. The disk member is positioned within the LCM test cell and represents a loss circulation zone in a subterranean zone in which a wellbore is drilled using the wellbore drilling fluid. An ability of the LCM to decrease loss circulation through the loss circulation zone is evaluated based on the flow of at least a portion of the LCM test material through the disk member.

This, and other aspects, can include one or more of the following features. To pressurize the LCM test material to flow through the disk member including the multiple openings, the disk member can be placed to the LCM test cell between an inlet to the LCM test cell and an outlet to the LCM test cell. A quantity of the LCM test material that flows from the inlet through the disk member through the outlet within a certain duration can be measured.

With or without any of the other aspects, to pressurize the LCM test material, a nitrogen pressure can be applied to pressurize the LCM test cell to flow the LCM test material toward the loss simulating disk member in the LCM test cell.

With or without any of the other aspects, to evaluate the ability of the LCM, a sealing efficiency of the LCM can be determined. The sealing efficiency is an ability of the LCM to prevent flow of a mixture of the wellbore drilling fluid through the plurality of openings in the disk member. The spacer fluid is sometimes used to prevent contamination of wellbore fluid due to the mingling action of the LCM slurry and the wellbore fluid at the interface.

With or without any of the other aspects, to flow the LCM test material to the LCM test cell, the drilling fluid reservoir, the LCM reservoir and the spacer fluid reservoir can be positioned on a first base member. The LCM test cell can be positioned on a second base member positioned vertically lower than the first base member relative to a floor on which the first base member and the second base member are positioned, the floor being below the first base member and the second base member. The LCM test material flows to the LCM test cell under gravity or under the action of an applied pressure if the LCM slurry is unable to flow under the action of gravity force.

With or without any of the other aspects, a first quantity of the drilling fluid or a second quantity of the spacer fluid or a third quantity of the LCM flowed to the LCM test cell can be controlled using a fluid transfer network that fluidically couples the drilling fluid reservoir, the spacer fluid reservoir and the LCM reservoir, and a valve network that controls flow of the drilling fluid, the spacer fluid and the LCM to the LCM test cell.

With or without any of the other aspects, the LCM test material can be pressurized to a pressure of substantially 2000 psi.

With or without any of the other aspects, the LCM test material can be flowed to the LCM test cell at a pressure of substantially 500 psi.

A loss circulation material (LCM) testing apparatus includes an LCM testing cell. The LCM testing cell includes an inlet. The inlet is configured to introduce a LCM testing fluid into the LCM testing cell. The LCM testing fluid is a slurry of LCM material and a wellbore drilling fluid. The LCM testing cell includes an outlet. The outlet is configured to pass the LCM testing fluid from the LCM test cell. A fluid flow pathway within the LCM testing cell is defined between the inlet and the outlet. The LCM testing cell includes a disk member that is removable. The disk member is positioned in the fluid flow pathway. The disk member includes a disk base and a plurality of downstream-directed extensions, which combined define a plurality of flow openings. Fluid flowing from the inlet to the outlet traverses through a plurality of flow openings in the disk member.

A method of evaluating a loss circulation material (LCM) includes the step of introducing a LCM testing fluid into the LCM testing cell. The LCM testing fluid traverses the disk member as previously described. The LCM testing fluid includes components as previously described. The method includes detecting an amount of LCM testing fluid traversing the LCM test cell.

The details of one or more implementations of the subject matter described in this specification are set forth in the accompanying drawings and the description later. Other features, aspects, and advantages of the subject matter will become apparent from the description, the drawings, and the claims.

BRIEF DESCRIPTION OF THE DRAWINGS

FIGS. 2A-2D are schematic diagrams of disk members, each with multiple openings.

Like reference numbers and designations in the various drawings indicate like elements.

DETAILED DESCRIPTION

Figure 1:
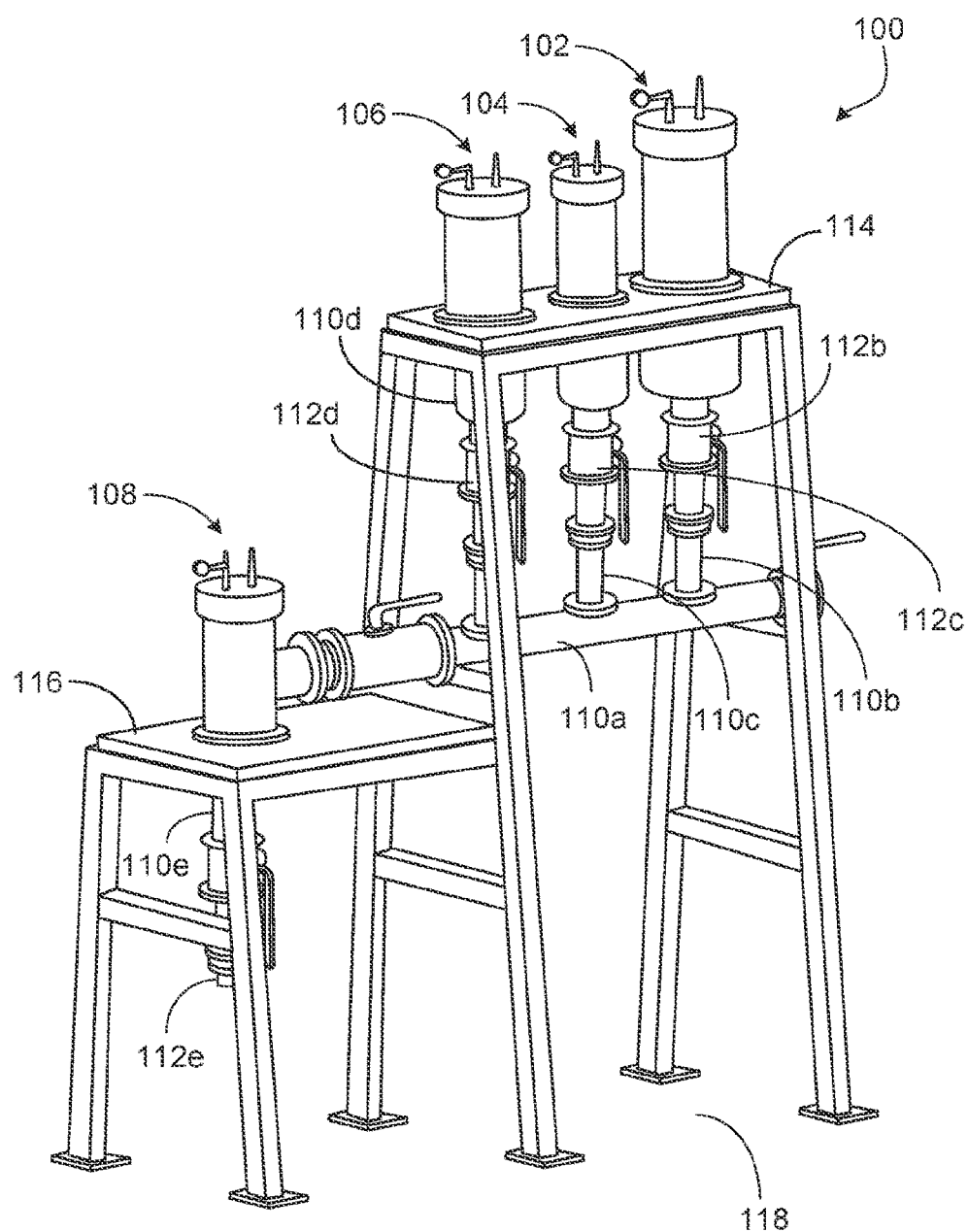
FIG. 1 is a schematic drawing of an example LCM test apparatus.

Lost circulation contributes to drilling non-productive time. Loss of circulation while drilling can range from seepage (low loss) to moderate or severe losses. When encountering a high-permeability, super-k, fractured, vugular or cavernous formation while drilling, a large volume of drilling mud can be lost into the formation with a quick drop of mud column in the wellbore. The drop of mud column can trigger drilling problems such as stuck pipe, wellbore instability, kick or blowout leading to side tracking or abandonment of a well. Addressing lost circulation along with the problems triggered by a loss circulation event can be expensive (for example, in the range of millions of dollars annually), with a portion of the costs being directed to the procurement of various LCMs to treat the seepage, moderate or severe loss zones.

LCMs are specifically designed to combat lost circulation. The design and development of LCMs involves performance evaluation using pore plugging tests performed in laboratories. A pore plugging test can be used to evaluate materials for seepage (that is, low losses) to moderate losses. In the pore plugging test, disks having openings (for example, slots) of different sizes (for example, 0.5 mm, 1 mm, 2 mm or a different size) are used to evaluate the LCM under given temperature and pressure conditions by flowing a mixture of the LCM and drilling fluid through the disks. The sizes of the openings correspond to the sizes of the fractures in the loss circulation zone in the subterranean zone. A pore plugging test using disks of the sizes described earlier are often insufficient to evaluate LCMs designed for severe loss zones because the sizes of the openings in the severe loss zones are greater than those in the seepage or moderate-type zones, rendering the disks described earlier ineffective or unsuitable.

This disclosure describes a design, development and method of use of a test apparatus for LCM performance evaluation, for example, for LCM designed for use in severe loss zones. The types of LCM that can be evaluated can include, for example, particulate type LCM, flake type LCM, fibrous LCM, various combination of particulate, flaky and fibrous LCMs, two component systems, rapid squeeze type LCMs, shaped LCMs, and the like. The evaluated LCM can be used in any type of loss circulation application, for example, severe or total loss of circulation. As described later, the test apparatus includes multiple components, for example, a test cell, a mud reservoir, a spacer or activator reservoir and a LCM reservoir. The components are engineered and assembled in a systematic way using various fixtures, for example, ball valves, relief valves, connecting pipes, pressure inlets, fluid outlets, disks with slotted and openings or holes (non-circular or circular in cross-section) to simulate various loss zones, and associated components. The test cell is configured to hold one or more of several disks, for example, metal disks with openings that represent a loss zone. In general, the disks can be made of materials that are resistant to the pressures within the reservoirs described later and chemically resistant to the fluids flowed through the disks. The openings can be slots (for example, up 40 mm in size) that represent a fractured loss zone or circular holes that represent vugular loss zones. In some implementations, the slots can be circular holes. Alternatively, or in addition, the slots can be non-circular. The diameters of the circular openings or the widths of the non-circular slots on the same disk can be the same or different.

As described later, the test apparatus can be used to test various LCM products up to a threshold working pressure (for example, up to 2000 pounds per square inch (psi)). The reservoir chambers, each of which includes the drilling fluid, spacer and LCM slurry, respectively, are individually connected to the test cell using fluid lines that can flow the respective fluid to the test cell at a flow pressure (for example, up to 500 psi). After flowing the desired material (for example, the LCM slurry and at least one of the drilling fluid or the spacer), the test cell can be sealed and the reservoirs can be closed. The test cell can then be pressurized for a duration (for example, 30 minutes or similar duration) by applying a working pressure up to or less than the threshold working pressure. The pressure causes the material in the test cell to flow through the disks in the test cell toward an outlet of the test cell. A quantity of material that flows out of the test cell within the test duration is collected to evaluate the performance of the LCM. After completing the test, the pressure from the test cell is released, the left over material is removed and the test apparatus is cleaned to prepare for a subsequent test.

Implementations of the subject matter disclosed in this specification can enable constructing a test apparatus for evaluation of LCM for extreme drilling conditions applicable in a loss circulation zone having vugs or large fractures (or both). Implementations can also enable testing the LCM. Implementations can also allow determining a suitability of a LCM to prevent or minimize lost circulation in severe loss zones, moderate loss zones or seepage zones.

FIG. 1 is a schematic drawing of an example LCM test apparatus 100. The apparatus 100 can be implemented to evaluate effectiveness of LCM for application in extreme drilling conditions in a loss circulation zone having vugs or large fractures (or both). For example, a zone with fractures larger than 10 mm or with vugs of diameter larger than 10 mm can lead to severe loss circulation. The apparatus 100 includes a drilling fluid reservoir 102 that can carry a wellbore drilling fluid, a spacer fluid reservoir 104 that can carry a spacer fluid, a LCM reservoir 106 that can carry a loss circulation material (LCM, specifically, the LCM to be evaluated) and a LCM test cell 108. The LCM test cell 108 includes a disk member 200 (FIG. 2A) that has multiple openings.

FIGS. 2A-2D are schematic diagrams of disk members, each with multiple openings. FIG. 2A shows the disk member 200 having a thickness T1 (for example, between 2 mm and 5 mm, for example, about 3 mm). The disk member 200 includes a circumferential sealing groove 204 *a*, for example, a groove to hold an O-ring or similar seal. FIG. 2B shows a disk member 202 having a thickness T2 greater than the thickness of T1. For example, the thickness T2 can range between for example 15 mm to 50 mm (for example, about 20 mm or about 40 mm). Such disks can have two circumferential sealing grooves 204 *b* and 204 *c* axially separated from each other. FIG. 2C is a schematic diagram showing circular openings. Each opening is a through hole that extends from one axial end face of the disk member to another. FIG. 2D is a schematic diagram showing non-circular openings. The arrangement of the openings (circular or non-circular) on the end faces that is shown in FIGS. 2C and 2D are examples. Other arrangements are possible. For example, the openings need not be symmetrically formed. The non-circular openings can be oriented in different directions. A disk member (such as the disk member 200) together with the multiple openings represents a loss circulation zone in a subterranean zone in which a wellbore is drilled using the wellbore drilling fluid.

As stated previously, vugular loss zones frequently encountered in carbonate formations rarely contain vugs of similar sizes. Hence, a test structure which includes a cluster of variably-sized openings may better represent the realistic subsurface condition of a vugular loss zone.

Figure 5A:
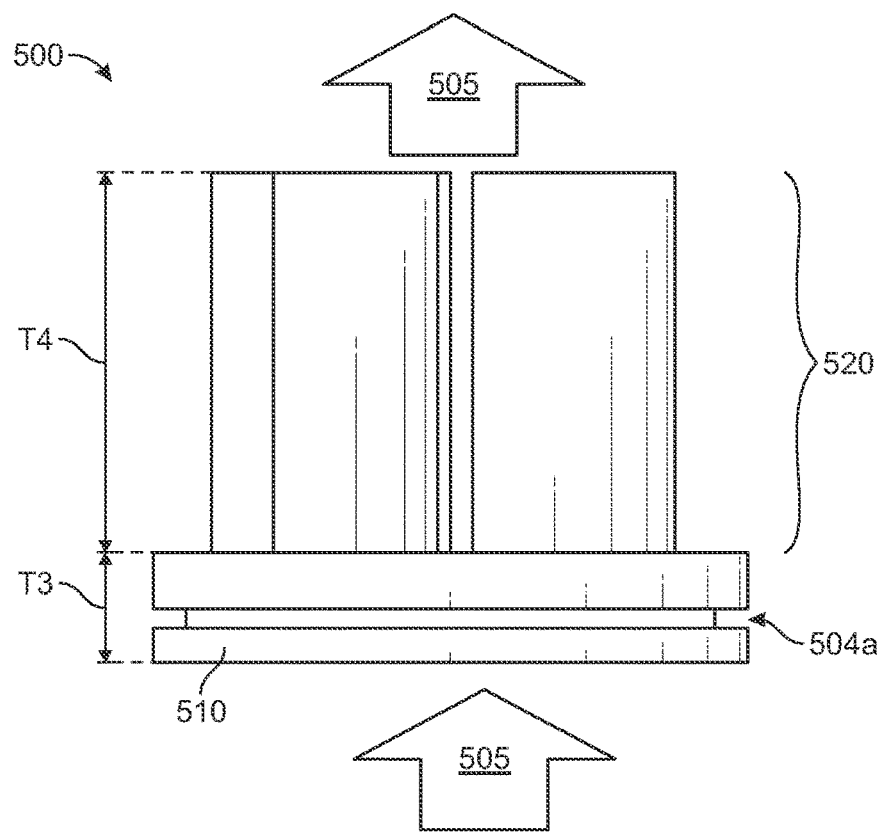
FIGS. 5A-5C are schematic diagrams of additional disk members.
Figure 5B:
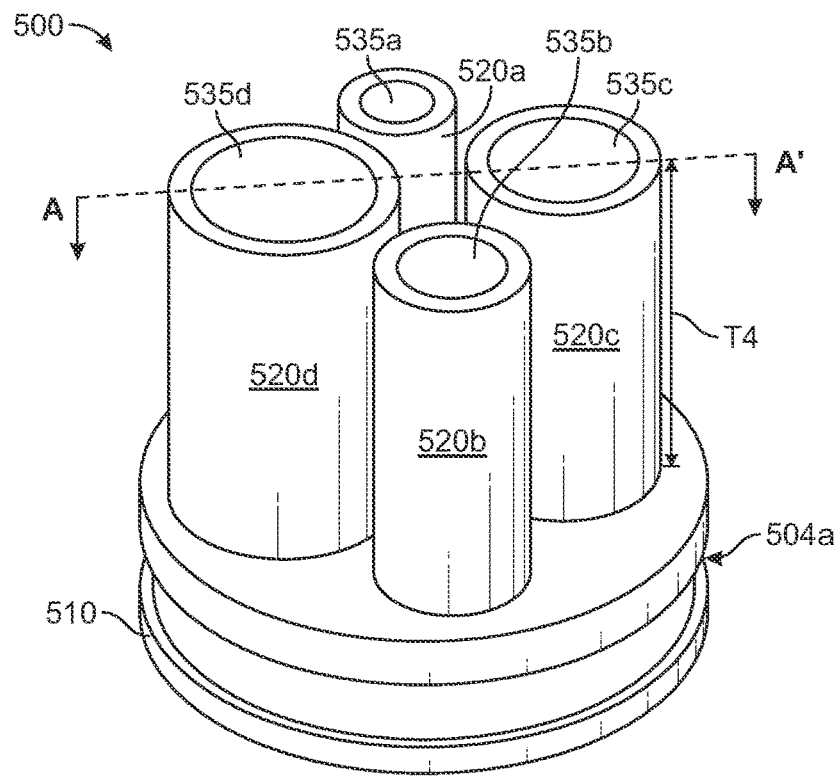
Figure 5C:
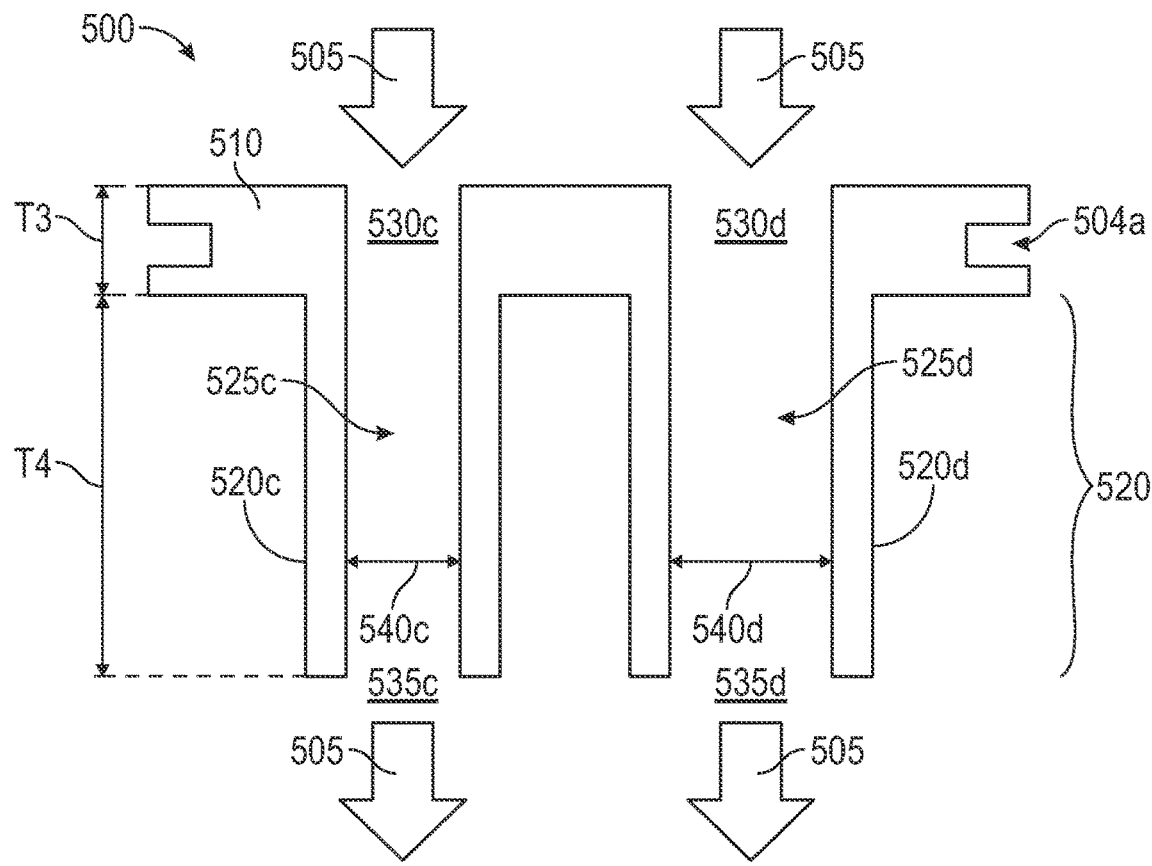

FIGS. 5A-5C are schematic diagrams of a side view, an isometric view, and a cross sectional view, respectively, of an embodiment of disk member 500 with multiple openings having multiple sizes for simulating a vugular loss zone.

FIG. 5A shows a side view of the disk member 500 having two major sections: a disk base 510 and a downstream-directed extensions 520. It is understood that disk member 500 is a singular and unitary device. As shown in FIG. 5A, a fluid flow 505 traverses through disk member 500 by first passing through disk base 510 and then through downstream-directed extensions 520. Disk base 510 represents a small cross-sectional area of the vugular loss zone. Disk base 510 has a thickness T3 (for example, in a range of from about 8 mm (millimeters) to about 12 mm, such as 10 mm). Downstream-directed extensions 520 in the embodiment shown in FIG. 5A embodiment has a single length T4 (for example, in a range of from about 40 mm to about 60 mm, such as 50 mm). Length T4 of downstream-directed extensions 520 may be greater than thickness T3 of disk base 510.

In some embodiments, the thickness T3 of the disk base 510 of disk member 500 may be greater than the overall thickness of disk member 200 as depicted in FIG. 2A. The disk member is positioned in a fluid flow pathway defined through the LCM testing cell between the inlet and the outlet of the LCM test cell. Test fluid flowing from the inlet to the outlet traverses through a plurality of flow openings in the disk member. The test fluid is a slurry of LCM material and a wellbore drilling fluid. Such a thickness (T3) of the disk base 510 of disk member 500 may allow for configurations of the disk member 500 to not only be overall stronger and more robust for a greater range of testing than the disk members previously described, especially for consideration under severe dual-phase flow conditions, but also for permitting for the configuration of realistic representations of the entry and opening of a flow pathway or opening for studying fluid and LCM interaction outside and within a vug, as will be described further.

A method of evaluating a loss circulation material (LCM) includes introducing an LCM testing fluid into a LCM testing cell. The LCM testing fluid traverses through a disk member. The disk member has a plurality of flow openings. The plurality of flow openings are defined in part by a plurality of downstream-directed extensions. As previously provided, the LCM testing fluid comprises a slurry of LCM material and a wellbore drilling fluid. The method includes detecting an amount of LCM testing fluid traversing the LCM test cell.

The disk member is removable from LCM test cell. As such, the disk base 510 may include a circumferential sealing groove 504 *a*, for example, a groove to hold an O-ring or similar seal. Such a sealing surface against the interior of the LCM testing cell prevents fluid bypass around the disk member during testing. Such disk bases 510 can have two or more circumferential sealing grooves axially separated from each other. One of ordinary skill in the art can appreciate that configurations of the disk base 510 that are not circular may have a sealing groove around the outermost edge of the disk base to provide a similar function of preventing fluid bypass around disk member 500. FIG. 5B depicts an isometric view of the disk member 500 of FIG. 5A. Disk base 510 having circumferential sealing groove 504 *a* is still visible.

FIG. 5B also shows disk member 500 having four downstream-directed extensions 520*a-d* connected to disk base 510. Each downstream-directed extension 520*a-d* in FIG. 5B has a length T4. The direction of the fluid flow is not depicted in FIG. 5B, but again fluid would first pass through disk base 510 and then through downstream-directed extensions 520*a-d*.

The embodiment of the disk member shown in FIG. 5B of disk member 500 has four openings. Specifically, these four openings are defined by the disk base 510 and downstream-directed extensions 520*a-d*. In this and other embodiments, having a plurality of openings to simulate multiple fluid flow pathways may be used to better represent the realistic subsurface conditions of a vugular loss zone upon interaction with mitigation materials.

Because of the isometric view of FIG. 5B, only downstream exits 535*a-d* of the four openings within downstream-directed extensions 520*a-d*, respectively, are visible.

FIG. 5C is a cross sectional view at dashed line AA' in FIG. 5B. Thus, FIG. 5C shows the internal configuration of the same disk member 500 in FIGS. 5A and 5B. As before, disk member 500 includes disk base 510 and downstream-directed extensions 520. Disk base 510 again includes circumferential sealing groove 504. Disk base 510 again has a thickness (T3) and downstream-directed extensions 520 has a length (T4). Due to the location of the cross section AA', only downstream-directed extensions 520 *c* and 520 *d* are visible within downstream-directed extensions 520. The arrows indicate the direction of fluid flow 505 through disk member 500.

Defined within disk base 510 and downstream-directed extensions 520*c* and 520*d* are two flow openings 525 *c*, 525 *d*. The flow openings 525 *c*, 525 *d* provide a fluid flow path through disk member 500 for fluid flow 505. Disk base 510 is on an upstream-facing side of disk member 500. Within flow openings 525 *c*, 525 *d*, fluid flow 505 traverses through disk base 510 before entering downstream-directed extensions 520*c*, 520*d*. Furthermore, fluid enters flow openings 525*c*, 525*d* via upstream entries 530 *c*, 530 *d*, respectively, and exits via downstream exits 535 *c*, 535 *d*, respectively.

Fluid flow path via flow openings 525*a-d* have an effective length of T3 (base thickness 510)+T4 (downstream-directed extensions 520*a-d*). In the instance of the embodiment shown in FIG. 5, the fluid flow path through disk member 500 may have a range of from about 48 mm to about 72 mm, such as about 60 mm.

In disk base 510 of disk member 500 on an upstream-facing side, there are two upstream entries 530 *c*, 530 *d* formed for the two visible flow openings 525 *c*, 525 *d*, respectively. Thus, upstream entries 530 *c*, 350 *d* provide fluid connectivity to the flow openings 525 *c*, 525 *d*. As with the entries being associated with the openings in which fluid and LCM are to traverse, so may there be a plurality of upstream entries formed in the disk base to accommodate the plurality of flow openings.

For the instance shown in FIG. 5, the upstream entries 530*a-d* may have a diameter or width in a range of from about 5 mm to about 20 mm.

Similarly, in downstream-directed extensions 520 of disk member 500 on a downstream-facing side, there are two downstream exits 535*c*, 535*d* formed for the two visible flow openings 525*c*, 525*d* respectively. Thus, downstream exits 535*c*, 535*d* provide fluid connectivity to flow openings 525*c*, 525*d*. As with the entries being associated with the openings in which fluid and LCM are to traverse, so may there be a downstream exit formed within each downstream extension to accommodate each of the plurality of openings.

The internal dimensions 540*c*, 540*d* of the flow openings 525*c*, 525*d* of downstream-directed extensions 520*c*, 520*d*, respectively, are indicated in FIG. 5C. The internal dimension 540*c*, 540*d* of each flow opening 525*c*, 525*d* is the largest distance than can be measured within openings flow 525*c*, 525*d*. Internal dimension 540*c* of flow opening 525*c* may be in a range of from about 14 mm to about 18 mm, for example, about 15 mm. Internal dimension 540*d* may be in a range of from about 18 mm to about 22 mm, for example, about 20 mm. Further, because the embodiment as shown in FIG. 5C has flow openings 525*c*, 525*d* that are roughly cylindrical, internal dimensions 540*c*, 540*d* are the diameter of flow openings 525*c*, 525*d*. Internal dimensions 540*c*, 540*d* for other potential conformations of the flow openings 525*c*, 525*d* as a whole are discussed further.

Disk member 500 may be fabricated from one or more materials. In some embodiments, the disk member comprises a singular material. In other embodiments, the disk member comprises a plurality of materials. Any combination of same and different materials for the disk member 500 may also be possible. In some embodiments, disk base 510 and all downstream-directed extensions 520a-d may be fabricated from the same material. In some embodiments, the disk base 510 and downstream-directed extensions 520a-d may perform different functions. Thus, different components of disk member 500 may be fabricated with different materials. In some embodiments, downstream-directed extensions 520a-d may be manufactured from one material and disk base 510 from a second material. When formed as separate components, one having skill in the art will appreciate that downstream-directed extensions 520a-d and disk base 510 may need to be joined in some fashion to form disk member 500, such as by bonding, adhesive, welding, and others Some of the materials that may be used to fabricate one or more embodiments of the disk member 500 include, but are not limited to, polymers, ceramics, glasses, or metals. In some embodiments, at least a portion of the disk member is made of a polymer. Some polymers may include, but are not limited to, polyethylenes (PE), including ultra-high-density PE polycarbonates (PC), polymethyl methacrylates (PMMA); polypropylenes (PP); polyvinyl chlorides (PVC); polystyrenes (PS), including high-impact PS; polyamides, including nylons, such as Nylon 12 and glass-filed nylons; silicones, Teflon® (polytetrafluoroethylene) and other fluoropolymers; thermoplastic polyurethanes (TPU); acrylonitrile-butadiene-styrene (ABS) triblock polymer; acrylic-styrene-acrylonitrile triblock polymer (ASA); polyaryletherketones (PAEK), polyether ether ketone (PEEK), polyetherimides (PEI), polyethylene terephthalate (PET); polylactides; and epoxy resins. In some embodiments, at least a portion of the disk member is made of a ceramic or a glass. Some example ceramics and glasses may include crystalline or glassy oxides, nitrides, silicates, and carbides, such as alumina, aluminosilicate glass, aluminum nitride, boron nitride, borosilicate glass, cordierite, Corning Pyrex®, graphite, lava (grade A), lead glass, Macor®, mullite, quartz, sapphire, porcelain, silicon, silicon carbide, silicon nitride, soda-lime glass, Steatite L-5®, and zirconia. In some embodiments, at least a portion of the disk member is made of a metal. Some example metals may include aluminum, brass, bronze, cobalt, chromium, copper, gold, platinum, steel, including stainless steel, silver, and titanium, and composites and alloys thereof, such as Monel and Inconel, and combinations thereof. Other specialized materials may be used, such as plastics that contain nanomaterials such as carbon nanotubes and nanofibers. Further, one having skill in the art will appreciate additional materials that may be used to fabricate disk member.

In one or more embodiments, the disk member may be fabricated via additive manufacturing processes. Additive manufacturing may be taken to mean any type of manufacturing process that builds a three-dimensional (3D) object from a computer-aided design model. Additive manufacture is also known in some instances as 3D printing; however, there is not the only form of additive manufacturing. For example, disk member 600 in FIG. 6 was produced using additive manufacturing.

A combination of additive and subtractive manufacturing may be used, in one or more embodiments. For example, one or more downstream-directed extensions 5620a-d may be fabricated via additive manufacturing, while the disk base 510 may be fabricated via using traditional manufacturing techniques, such as molding or milling from a larger piece via CAD/CAM (computer-aided design/computer-aided manufacturing).

The LCM test cell is configured to be pressurized upstream of the disk member to a pressure in a range of from about atmospheric pressure to about 2000 pounds per square inch (psi). However, it is within the realm of vision that an embodiment LCM test cell may be configured to generate a pressure upstream of the disk member up to about 3000 psi, up to about 4000 psi, and up to about 5000 psi. In some embodiments, the disk member is configured to tolerate a pressure differential between the upstream side and the downstream side of the disk member in a range from about 0 to about 2000 pounds per square inch differential (psid). For example, the disk member 600, which is fabricated from ABS, is operable to withstand a differential pressure in a range of greater than about 0 psid to about 100 psid. Other, materials, including metallic-fabricated versions of the disk member, may tolerate differential pressures well in excess of 2000 psid, such as up to 3000 psid. One of ordinary skill in the art may envision the management of upstream and downstream (back) pressures to foster the appropriate testing environment conditions for the LCM testing fluid with the disk member.

In embodiments of the method, the method may include the step of applying pressure to the LCM testing fluid upstream of the disk member. In some such embodiments, the pressure is maintained upstream of the disk member in a range of from about greater than atmospheric pressure to about 2000 psi. In some such embodiments, a pressure differential between the portion of the LCM testing cell upstream of the disk member and downstream of the disk member is maintained in a range of from about 0 to about 2000 psid.

In some embodiments, the disk member is fabricated of a material that is chemically resistant to any corrosive effects of the LCM test fluid. The disk member can be constructed of a material that is chemically resistant to the LCM test fluid flowed through the cell. For example, the disk member material can be resistant to the corrosive effects of the LCM test fluid flowed through the cell. A wellbore drilling fluid or a spacer fluid as part of the LCM test fluid itself may facilitate corrosion, for example, a seawater or brine based fluid. As well, additives incorporated with the wellbore drilling fluid or a spacer fluid, including water, acids, and alkaline agents, may promote corrosion. Non-limiting examples of useful corrosion-resistant polymer materials for fabricating a disk member may include polyvinyl chloride (PVC), polytetrafluoroethylene (PTFE), and polypropylenes (PP). Non-limiting examples of useful corrosion-resistant metallic materials may include carbon steel, galvanized steel, stainless steel, aluminum and various alloys thereof. Such materials are also excellent at withstanding the impact of the slurry as it traverses through the disk member at high differential pressures.

In some embodiments of the method, the LCM testing fluid further comprises a spacer fluid.

In some embodiments, at least a portion of the disk member is non-opaque. One or more components of disk member may be fabricated from a non-opaque material, such as a transparent material or a semi-transparent material. A few examples of non-opaque materials that may be used to fabricate one or more components of disk member include aluminosilicate glass, borosilicate glass, Corning Pyrex®, Macor®, PC, PMMA, quartz, soda-lime glass, and aluminum oxynitride. Use of a non-opaque material may allow for the study the interactions between the LCM and disk member 500 during fluid flow either while fluid is flowing or after the flow has stopped. In some embodiments, studying this interaction may include studying the movement of LCM that is passing through the disk member. In some embodiments, studying the interaction may include studying the stacking of the LCM within the disk member. In some embodiments, the at least a portion of the disk member is at least one downstream-directed extension. One or more downstream-directed extensions may be fabricated from a non-opaque material while the disk base may be fabricated from a stronger or more resilient yet opaque material.

In some embodiments of the method, the step of detecting an amount of LCM testing fluid traversing the LCM test cell comprises visually monitoring the LCM interacting with the disk member. At such instances, at least a portion of the disk member is non-opaque.

Figure 6:
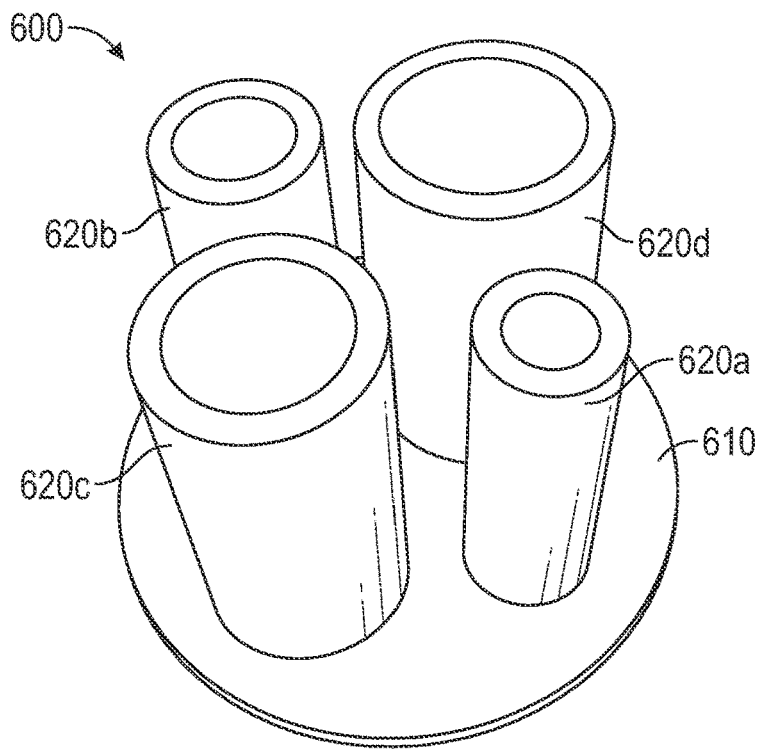
FIG. 6 is a photograph of a disk member.

FIG. 6 depicts a photograph of an embodiment of such a disk member 600. Disk member 600 has two major parts: a disk base 610 and four downstream-directed extensions 620a-d. Downstream extension 620 a has a flow opening with an internal dimension of about 10 mm. Downstream extension 620 b has a flow opening with an internal dimension of about 15 mm. Downstream extension 620 c has a flow opening with an internal dimension of about 20 mm. Downstream extension 620 d has a flow opening with an internal dimension of about 25 mm. The length (T4) of each of the four downstream-directed extensions 620a-d is about 50 mm. The thickness (T3) of disk base 610 is about 3 mm.

Disk member 600 of FIG. 6 was completely fabricated with additive manufacturing using ABS. Using additive manufacturing may be beneficial for a number of reasons. First, the forms created by additive manufacturing are first generated in a computer and then "printed" using some type of computer-controlled layer-by-layer fabrication technique. Thus, the computer-aided design process may enable iterative design of the disk member 500. Furthermore, the source files used in additive manufacture may be based upon 3D scans of natural geologic formations or on 3D artists renderings of naturally-inspired or artificial shapes. As a result, disk base 610 and downstream-directed extensions 620a-d, and particularly the openings within (not depicted) may closely simulate natural geologic formations.

The layer-by-layer nature of additive manufacturing allows one to form geometries that are impossible to create using traditional subtractive manufacturing. Thus, additive manufacturing may allow, for example, disk base 610 and downstream-directed extensions 620a-d to have more complex shapes while being a single, integrated unit. Thus, the openings within (not depicted made take the shapes of more complex configurations that may not be formed using traditional subtractive manufacturing.

Additive manufacturing is often faster and more adaptable than traditional subtractive manufacturing. Thus, additive manufacturing may allow one to quickly fabricate a series of disk members with varied geometries to enable experimental studies of things like the impact of opening size. Additionally, decreased fabrication time may allow a researcher to fabricate and evaluate an initial 3D prototype of disk member before fabricating a final disk member for use in experiments.

Figure 7A:
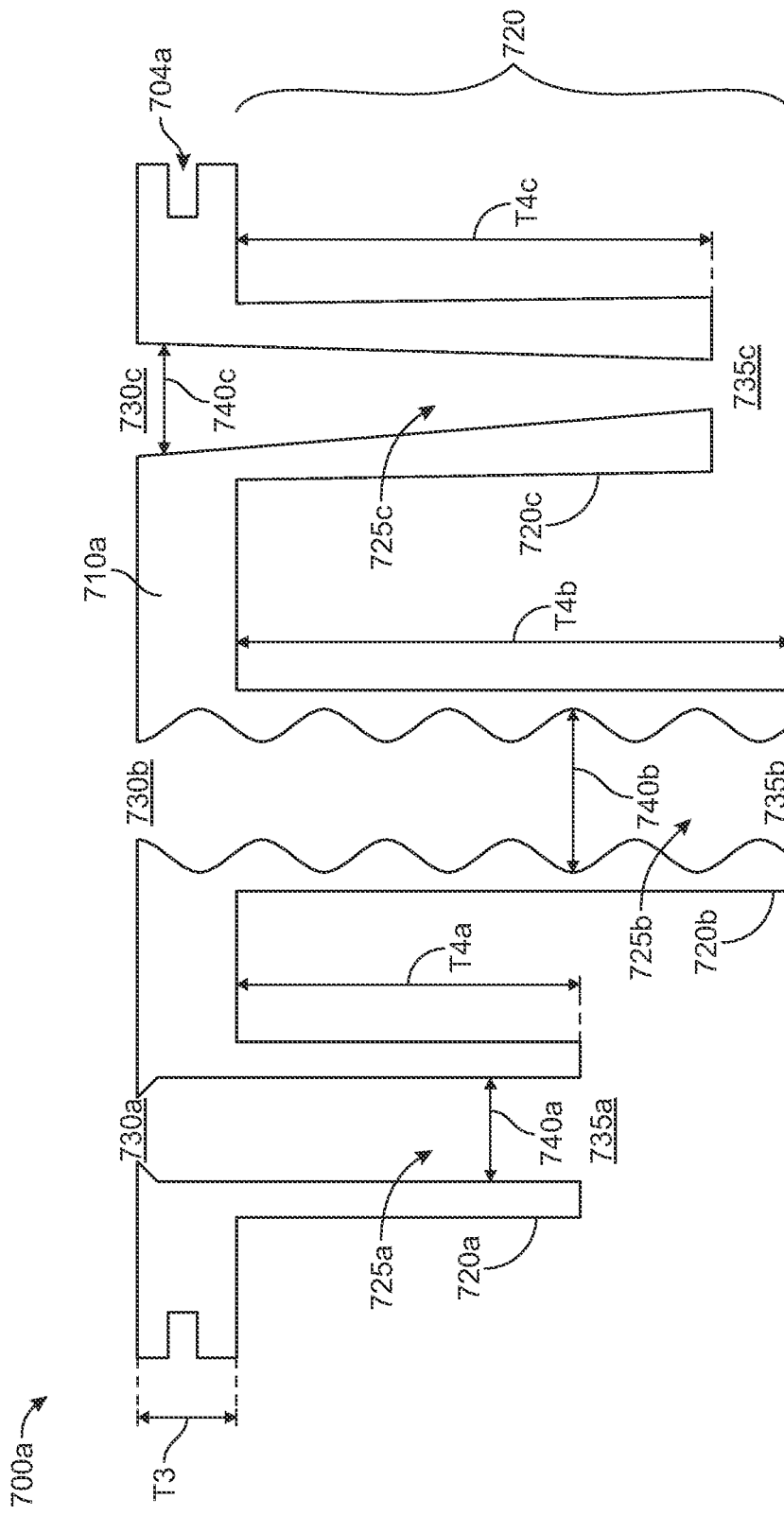
FIGS. 7A-7B are schematic diagrams of additional disk members.
Figure 7B:
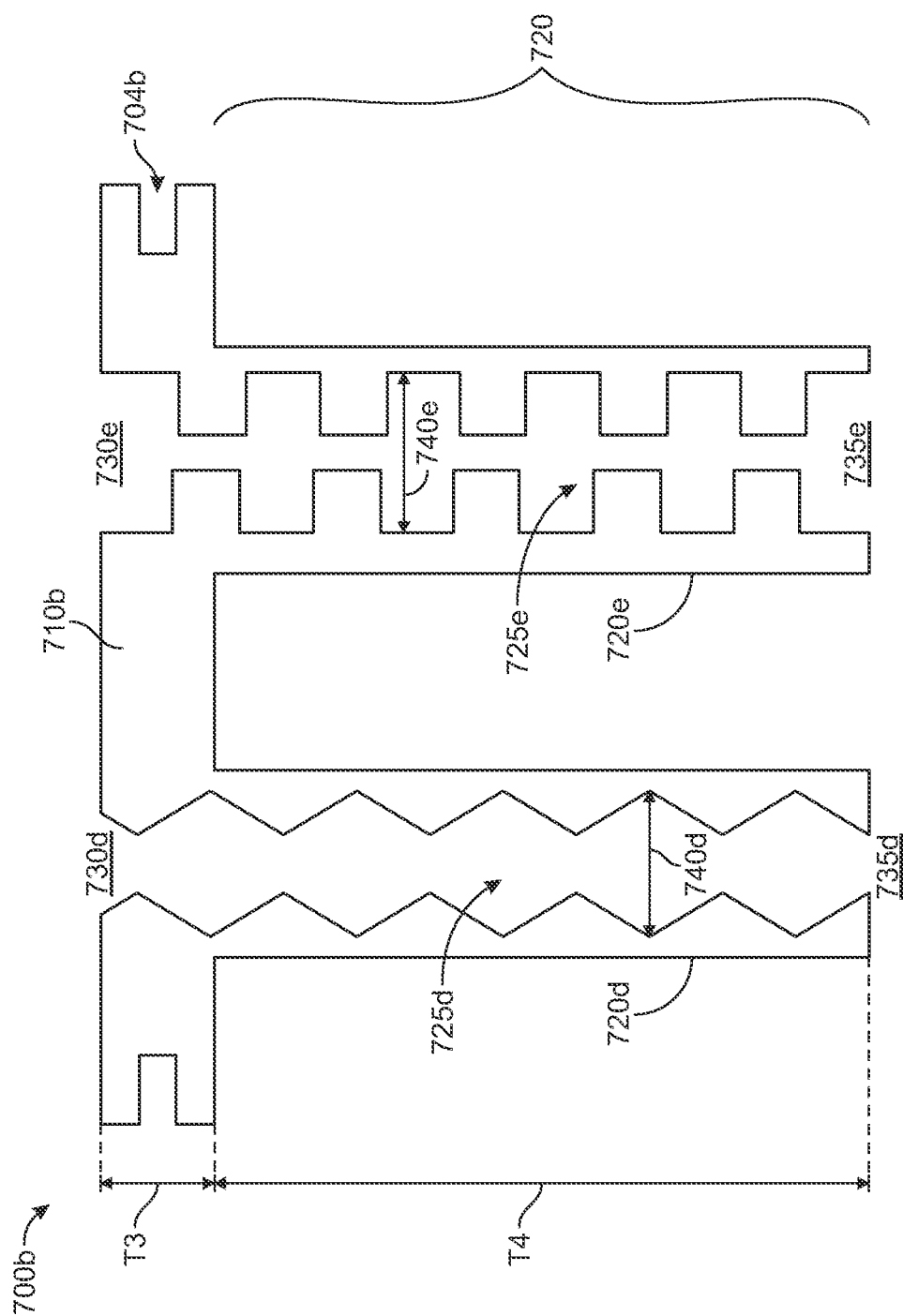

FIGS. 7A and 7B depict cross-sections of two additional disk members 700 a, 700 b, respectively. A disk base 710 a, 710 b and downstream-directed extensions 720 are indicated. Each disk base 710 a, 710 b includes a circumferential sealing groove 704a, 704 b. In FIG. 7A, each flow opening 725a-c is defined by disk base 710 a and one of the downstream-directed extensions 720a-c, respectively. In FIG. 7B, each flow opening 725 d, 725 e is defined by disk base 710 b and one of the downstream-directed extensions 720 d, 720 e, respectively. As previously, disk base 710 a, 710 b has a thickness T3. Downstream-directed extensions 720a-c have a length of T4a-c, respectively. Downstream-directed extensions 720 d, 720 e have a thickness of T4.

Each flow opening 725a-e has a different configuration along its length T3+T4. For the sake of simplicity, flow opening 725a-e are rotationally symmetric; however, this need not be the case. However, flow openings 725a-e may or may not be rotationally symmetric in one or more embodiments. In some embodiments, the configuration of each flow opening may be irregular or non-symmetrical. For example, in the simulation of a vug irregularities may be introduced to better understand the impact of such structural anomalies to slurry flow.

In FIG. 7A, disk base 71a has three upstream entries 730a-c. In FIG. 7B, disk base 710 b has two upstream entries 730 d, 730 e. Each disk extension 720a-e has a downstream exit 735a-e, respectively. The largest dimension in flow opening 725a-e defines an internal dimension 740a-e, respectively.

Consider together FIGS. 5A-5C and 7A-7B. Various features depicted will be used to illustrate certain aspects of the one or more embodiments.

The configuration of the downstream exits and upstream entries may take any geometric form. Downstream exits may be round, oval, square, hexagonal, slit, crack, triangular, polygonal, or have any other regular or irregular shape. Similarly, upstream entries may be round, oval, square, hexagonal, slit, crack, triangular, polygonal, or have any other regular or irregular shape.

For the embodiment shown in FIGS. 5A-5C, the configuration of all downstream exits 535a-d and all upstream entries 530a-d are approximately circular. Although not shown in FIGS. 5A-C, all four fluid openings 525a-d are approximately cylindrical. All upstream entries 530a-d have approximately circular openings to those of 530c, 530d. All downstream exits 535a-d have the same shape. In the embodiment shown in FIG. 5, the configuration of the downstream exits 535a-d is the same as the configuration of the upstream entries 530a-d.

In some embodiments, for the plurality of flow openings there is at least a first flow opening and a second flow opening, a first flow opening has a first upstream entry configuration in the disk base that is the same or similar to that of a second upstream entry configuration for the second flow opening. In some embodiments, all of the upstream entry configurations are the same or similar. For example, in FIGS. 5A-C the plurality of upstream entries 530a-d have a similar uniform configuration of shape. Such uniformity may permit a simulation of how the entry to a flow opening is modified by the formation of the wellbore from its natural condition.

In some other embodiments, for the plurality of flow openings there is at least a first flow opening and a second flow opening, the first flow opening has a first upstream entry configuration in the disk base that is different than the second upstream entry configuration for the second flow opening. In some embodiments, all of the upstream entry configurations are different. For example, in FIG. 7A the upstream entries 730a, 730b may be different from one another. For example, the upstream entry 730b may represent a continuation of the shape or configuration of the flow opening 725b itself. The upstream entry 730a may have a shape or configuration that is dissimilar from the shape or configuration of the flow opening 725a itself.

In some embodiments, for the plurality of flow openings there is at least a first flow opening and a second flow opening, the first flow opening has a first downstream exit configuration in a first downstream-directed extension that is the same or similar to that of a second downstream exit configuration for a second downstream-directed extension for the second flow opening. In some embodiments, all of the downstream exit configurations are the same or similar. For example, in FIGS. 5A-C, the configuration of the downstream exits 535a-d on the downstream side of the downstream-directed extensions 520a-d may be similar or uniform in nature.

In some other embodiments, for the plurality of flow openings there is at least a first flow opening and a second flow opening, the first flow opening has a first downstream exit configuration in a first downstream-directed extension that is different than a second downstream exit configuration for a second downstream-directed extension for the second flow opening. In some embodiments, all of the downstream exit configurations are different. For example, the downstream exits 735b, 735c of FIG. 7A may represent a continuation of the shape or configuration of the flow openings 725 b, 725 c as defined by downstream-directed extensions 720b, 720c, but the configuration of both downstream exits 73 b, 735c are different from each other.

In some embodiments, for the plurality of flow openings there is at least a first flow opening having a first upstream entry configuration in the disk member and a first downstream exit configuration in a first downstream-directed extension, the first upstream entry configuration and the first downstream exit configuration are similar or the same. In some embodiments, all of the upstream entry configurations in the disk member and all of the downstream exit configurations in all of the downstream-directed extensions are the same or similar. For example, for the embodiment shown in FIGS. 5A-5C the shape of the downstream exits 535a-d in the disk member 510 is the same as the shape of the upstream entries 530a-d in the associated downstream-directed extensions 520a-d. In some embodiments, the configuration of the downstream exits 535a-d may match that of the upstream entries 530a-d.

In some other embodiments, for the plurality of flow openings there is at least a first flow opening having a first upstream entry configuration in the disk member and a first downstream exit configuration in a first downstream-directed extension, the first upstream entry configuration and the first downstream exit configuration are different. In some embodiments, all of the upstream entry configurations in the disk member and all of the downstream exit configurations for all of the downstream-directed extensions are different. For the embodiments shown in FIG. 7A, the shape of downstream exit 735b is not the same configuration of the shape for upstream entry 730b. The same can be stated for downstream exit 735d and upstream entry 730d in FIG. 7B.

In some embodiments, for the plurality of flow openings having an associated plurality of upstream entries, the plurality of upstream entries are uniformly distributed on the upstream-facing side of the disk base. For the example shown in FIGS. 5B and 5C, the upstream entries 530c, 530d to the flow openings 525c, 525d are closely and approximately regularly-spaced on disk base 510. Despite the different internal dimensions of flow opening 525c, 525d, the center of each upstream entry 530c, 530d is approximately located on a regular grid.

In some other embodiments, for the plurality of flow openings having an associated plurality of upstream entries, the plurality of upstream entries are irregularly distributed on the upstream-facing side of the disk base. In the example shown in FIG. 7A, the spacing between the upstream entries 730a-c on disk base 710a is non-uniform; rather, it is not regularly spaced. In some such other embodiments, the spacing between the upstream entries on the upstream-facing side of disk base may not be patterned, as if observed from the upstream-facing side of the disk base. Such configurations may be considered varied, random, or irregular to one of ordinary skill in the art. Such a non-regular pattern of upstream entries may be more reflective of actual vug configurations in nature.

In some embodiments, for the plurality of flow openings there is at least a first flow opening and a second flow opening, the first flow opening having a similar or the same configuration as the second flow opening. In some embodiments, all of the flow opening have the same configuration. In the example depicted in FIGS. 5A-5C, the exterior surfaces of downstream-directed extensions 520a-d are approximately cylindrical. Each downstream-directed extension internally defines a void. For the embodiment of FIGS. 5A-C, each downstream-directed extension 520a-d internally forms a void—the flow openings 525a-d, respectively—that are configured as if in a cylinder-like shape.

In other such embodiments, for the plurality of flow openings there is at least a first flow opening and a second flow opening, and where the first flow opening has a different configuration than the second flow opening. In some embodiments, all of the flow opening have a different configuration from each other. In the embodiments depicted in FIGS. 7A and 7B, the exterior surfaces of downstream-directed extensions 720a-e are approximately cylindrical. However, flow openings 725a-e each have a different configuration. Downstream-directed extension 720a defines a flow opening 725a that is roughly cylindrical-like shape with an upstream entry 730a with a smaller different size, similar to an orifice-like opening. Downstream-directed extension 720b defines a flow opening 725b that has undulating, sinusoidal wave-like shape. Downstream-directed extension 720c defines a flow opening 725c that has a cone-like shape that narrows towards the downstream direction. Downstream-directed extensions 720d defines a flow opening 725 d that has a zig-zag or triangular wave-like shape. Downstream-directed extensions 720 e defines a flow opening 725 e that has a boxy undulation or square wave-like shape.

In some embodiments, for the plurality of flow openings there is at least a first flow opening, a first flow opening having a first upstream entry configuration in the disk base that is complimentary in shape to the configuration of the first flow opening. In some embodiments, all of the upstream entry configurations are complimentary in shape to the configurations of the associated flow openings.

In some embodiments, for the plurality of flow openings there is at least a first flow opening, a first flow opening having a first downstream exit configuration in the downstream-directed extension that is complimentary in shape to the configuration of the first flow opening. In some embodiments, all of the downstream exit configurations are complimentary in shape to the configurations of the associated flow openings.

In some embodiments, both the first upstream entry and the first downstream exit configurations are complimentary in shape to the configuration of the first flow opening. In some embodiments, all of the upstream entry and the downstream exit configurations are complimentary in shape to the configuration of the associated flow opening.

In some embodiments, for the plurality of flow openings there is at least a first flow opening, a first flow opening having a first upstream entry dimension in the disk base that is the same or similar as the interior dimension of the first flow opening. In some embodiments, all of the upstream entry dimensions are the same or similar to the interior dimension of the associated flow openings.

In some embodiments, for the plurality of flow openings there is at least a first flow opening, a first flow opening having a first downstream exit dimension in the downstream-directed extension that is the same or similar as the interior dimension of the first flow opening. In some embodiments, all of the downstream exit dimensions are the same or similar to the interior dimension of the associated flow openings.

In some embodiments, both the first upstream entry and the first downstream exit dimensions are the same or similar to the interior dimension of the first flow opening. In some embodiments, all of the upstream entry and the downstream exit dimensions are the same or similar to the interior dimension of the associated flow openings.

In the example depicted in FIGS. 5A-5C, the upstream entries 530c, 530d and the downstream exits 535c, 535d have a complementary shape and similar dimension to the configuration and internal dimensions of the flow openings 525c, 525d to which they are associated. In the example depicted in FIGS. 5A-5C, internal dimension 540c of flow opening 525c is equal to the dimension of both upstream entry 530c and downstream exit 530c. Further, because flow openings 525c, 525d are roughly cylindrical, internal dimensions 540c, 540d, respectively, are the diameter of flow openings 525c, 525d. In some embodiments, the configuration both the upstream entry 530c and the downstream exit 530c for a flow opening may have equal dimensions. For example, FIG. 5C shows both the upstream entry 530c and the downstream exit 530c for a flow opening may have equal dimensions. As well, FIG. 7B shows not only the upstream entry 730e and the downstream exit 735e for a flow opening 725e having similar or equal dimensions, but also that their dimensions are also the same as internal dimension 740e.

In some embodiments, for the plurality of flow openings there is at least a first flow opening, a first flow opening having a first upstream entry configuration in the disk base that is not complimentary in shape to the configuration of the first flow opening. In some embodiments, all of the upstream entry configurations are not complimentary in shape to the configurations of the associated flow openings.

FIG. 7A shows upstream entry 730a having a configuration that is not complementary in shape to the configuration of flow opening 740a. Although upstream entry 730a appears circular in nature as does the diameter of flow opening 740a, the abrupt flow transition from a smaller dimension to a larger internal dimension does not represent a continuation of the configuration of flow opening 740a. The orifice-like configuration of upstream entry 730a may have a disruptive flow impact meriting study. Such a difference in configuration may be useful in representing a vug that has had the inlet to its natural configuration modified or altered by wellbore creation, modification or treatment activities.

In some embodiments, for the plurality of flow openings there is at least a first flow opening, a first flow opening having a first downstream exit configuration in the downstream-directed extension that is not complimentary in shape to the configuration of the first flow opening. In some embodiments, all of the downstream exit configurations are not complimentary in shape to the configurations of the associated flow openings.

In some embodiments, neither the first upstream entry nor the first downstream exit configurations are complimentary in shape to the configuration of the first flow opening. In some embodiments, none of the upstream entry and the downstream exit configurations are complimentary in shape to the configurations of the associated flow opening.

In some embodiments, for the plurality of flow openings there is at least a first flow opening, a first flow opening having a first upstream entry dimension in the disk base that is not the same or similar as the interior dimension of the first flow opening. In some embodiments, none of the upstream entry dimensions are the same or similar to the interior dimension of the associated flow openings.

In some embodiments, for the plurality of flow openings there is at least a first flow opening, a first flow opening having a first downstream exit dimension in the downstream-directed extension that is not the same or similar as the interior dimension of the first flow opening. In some embodiments, none of the downstream exit dimensions are the same or similar to the interior dimension of the associated flow openings.

In some embodiments, neither the first upstream entry nor the first downstream exit dimensions are the same or similar to the interior dimension of the first flow opening. In some embodiments, none of the upstream entry and the downstream exit dimensions are the same or similar to the interior dimension of the associated flow openings.

In FIG. 7A, internal dimension 740b of flow opening 725b is not equal to either the dimension of upstream entry 730b nor of downstream exit 730b. Internal dimension 740c of flow opening 725c is equal to the dimension of upstream entry 730b but is not equal to the dimension of downstream exit 730c. In some embodiments, when connected by a flow opening 725b, 725c, an associated upstream entry 730b, 730c and an associated downstream exit 735b, 735c may not have similar dimensions. Further, in some embodiments, neither upstream entry 730b, 730c nor downstream exit 735b, 735c may have a dimension that equals the internal dimension 740b, 740c of flow opening 725b, 725c, respectively.

In the example depicted in FIGS. 7A-B, the upstream entries 730b-d and the downstream exits 735b-d have a complementary shape but not a similar dimension to the flow openings 725b-d, respectively. In the example depicted in FIGS. 7A-B, the upstream entries 730b-d and the downstream exits 735b-d have a complementary shape but not a similar dimension 740c, 740d to the interior dimension 740c, 740d of flow openings 725c, 725d, respectively. In some embodiments, a flow opening associated with an upstream entry and a downstream exit may have not similar or same dimensions. For example, FIG. 7A shows flow opening 725c having upstream entry 730 and downstream exit 735c, where the interior dimension 740c is not similar either upstream entry 730 and downstream exit 735c at any point along its flow length.

The apparatus of claim 1, where for the plurality of flow openings there is at least a first flow opening and a second flow opening, and where the first flow opening has an associated first upstream entry with a first dimension and the second flow opening has an associated second upstream entry with a second dimension, where the first dimension and the second dimension are not the same or similar. In some embodiments, all the flow openings have an associated upstream entry and each upstream entry has a dimension, and where all the dimensions are not the same or similar. In FIGS. 5A-C, internal dimension 540c is less than internal dimension 540d; the dimension of upstream entry 530c is less than the dimension of upstream entry 530d. Thus, although flow openings 525c, 525d have similar configurations, flow openings 525c, 525d have different internal dimension 540c, 540d. In some embodiments, flow openings 525c, 525d within the same disk member 500 may have different dimensions. In some embodiments, flow openings 525c, 525d within the same disk member 500 may have the same or similar dimensions and internal dimensions.

In an embodiment, for a plurality of flow openings there is at least a first flow opening and a second flow opening, and where for the first flow opening has a first flow length that is the same or similar to a second flow length for the second flow opening. In some embodiments, all of the flow lengths for all of the flow openings for a disk member are the same or similar. As discussed previously, disk base has a thickness (T3). In FIGS. 5A-5C, downstream-directed extensions 520a-d each have a similar length (T4). Thus, as previously stated, an overall length of the flow pathway through disk member is T3+T4.

In some embodiments of the disk member, each of the plurality of flow openings has a flow length in a range of from about 3 mm (millimeters) to about 70 mm. In some such instances, the flow length is in a range of from about 40 mm to about 70 mm. One of skill in the art may envision that the flow length of an associated flow opening may be even longer than 70 mm; however, one may also need to accommodate the configuration of the LCM testing apparatus to facilitate such lengths while also respecting the other functional aspects of the LCM testing cell, including but not limited to overall apparatus size, ease of use and handling of cells operable for pressurization and supporting significant pressurization differentials, slurry mass and the forces of the flowing fluids and solids within, into and out of the apparatus.

In some instances, the overall flow length of a given disk member may vary depending on the variety of lengths of a plurality of downstream-directed extensions, each potentially having a different length (T4). In another embodiment, for a plurality of flow openings there is at least a first flow opening and a second flow opening, and where for the first flow opening has a first flow length that is different from a second flow length for the second flow opening. In some embodiments, all of the flow lengths for all of the flow openings for a disk member are different. For example, in FIG. 7A, the disk base 710a has a thickness of T3. In FIG. 7A, downstream-directed extensions 720a-c have different thicknesses T4a-c, respectively. Thus, each flow opening 725a-c has a different flow length, respectively. For example, flow opening 725a has a flow length of T3+T4a; flow opening 725b has a flow length of T3+T4b; flow opening 725c has a flow length of T3+T4c. FIG. 7A shows the flow opening 725a have a length less than flow opening 725c. In some embodiments, the flow length for each flow opening 725a, 725b, 725c in a disk member 700a may be a plurality of flow lengths.

In some embodiments of the method, the method further includes the step of determining a sealing efficiency of the LCM. Determination of the sealing efficiency is described following.

Each reservoir has an open volume in which the respective fluid can be carried. For example, the drilling fluid reservoir 102 can have a larger fluid-carrying volume compared to the LCM reservoir 106, which, in turn, can have a larger fluid-carrying volume compared to the spacer fluid reservoir 104. The LCM test cell can also have an open volume in which the LCM test material can be carried. The LCM test material includes a quantity of the LCM and a quantity of either the drilling fluid or the spacer fluid or both. The different fluid-carrying volumes can range between a few hundred milliliters (mL) and a few liters (L). In some implementations, each reservoir and the LCM test cell can have a substantially cylindrical fluid-carrying volume. A substantially cylindrical volume is a volume enclosed by a structure or surface that is cylindrical in shape within manufacturing tolerances. Other cross-sections are also possible.

Each reservoir and the LCM test cell can be constructed of a material that can withstand pressure (for example, greater than 500 psi and up to 3000 psi). For example, the material can be stainless steel. In general, the LCM test cell can be constructed of a material that is chemically resistant to the fluids flowed through the cell. For example, the LCM test cell material can be resistant to the corrosive effects of the fluids flowed through the cell.

The LCM test cell 108 is fluidically connected to the drilling fluid reservoir 102, the spacer fluid reservoir 104 and the LCM reservoir 106 using a fluid transfer network and a valve network. The fluid transfer network includes a first elongate tubular member 110 a fluidically coupled to the LCM test cell 108. The valve network includes a first valve 112 a in a flow path through the first elongate tubular member 110 a. A second elongate tubular member 110 b of the fluid transfer network fluidically couples the drilling fluid reservoir 102 to the first elongate tubular member 110 b. A second valve 112 b of the valve network in a flow path of the second elongate tubular member 110 b controls flow of the wellbore drilling fluid from the drilling fluid reservoir 102 through the second elongate tubular member 110b and further to the first elongate tubular member 110 a for flow to the LCM test cell 108. A third elongate tubular member 110 c of the fluid transfer network fluidically couples the spacer fluid reservoir 104 to the first elongate tubular member 110 a. A third valve 112 c of the valve network in a flow path of the third elongate tubular member 110 c controls flow of the spacer fluid from the spacer fluid reservoir 104 through the third elongate tubular member 110 c and further to the first elongate tubular member 110 a for flow to the LCM test cell 108. A fourth elongate tubular member 110 d of the fluid transfer network fluidically couples the LCM reservoir 106 to the first elongate tubular member 110 c. A fourth valve 112 d of the valve network in a flow path of the fourth elongate tubular member 110 d controls flow of the LCM from the LCM reservoir 106 through the fourth elongate tubular member 110 d and further to the first elongate tubular member 110 a.

In some implementations, the apparatus 100 includes a first base member 114 supporting the drilling fluid reservoir 102, the LCM reservoir 106 and the spacer fluid reservoir 104. For example, the first base member 114 can be a substantially horizontal board or plate on which the three reservoirs are arranged adjacent to each other. A substantially horizontal board or plate is a board or plate that has a surface that is horizontal relative to the floor and within manufacturing tolerances. The apparatus 100 also includes a second base member 116 supporting the LCM test cell 108. For example, the second base member 116 is can be a substantially horizontal board or plate positioned vertically lower than the first base member 114 relative to a floor 118 on which the first base member 114 and the second base member 116 are positioned. The arrangement allows fluid transfer to the LCM test cell 108 using gravity and without the need for a pump. Alternatively, a pump can be used to apply pressure to flow the fluid through the LCM test cell 108. In such implementations, the first base member 114 and the second base member 116 can be at substantially the same elevation from the floor 118 or the first base member 114 can be nearer to the floor 118 than the second base member 116. A substantially same elevation means that difference in a distance from the floor 118 of the first base member 114 and a distance from the floor 118 of the second base member 116 is within a deviation of no more than 5%.

For example, the first base member 114 can include respective openings through which the drilling fluid reservoir 102, the spacer fluid reservoir 104 and the LCM reservoir 106 are passed. The reservoirs can be vertically positioned in the respective openings such that inlets to the reservoirs face upward (that is, away from the floor 118) and the outlets face downward (that is, towards the floor 118). Ends of the second, third and fourth elongate tubular members (110 b, 110 c and 110 d, respectively) connect to the downward facing outlets of the drilling mud reservoir 102, the spacer fluid reservoir 104 and the LCM reservoir 106, respectively. Opposing ends of the second, third and fourth elongate tubular members (110 b, 110 c and 110 d, respectively) connect to the circumferential surface of the first elongate tubular member 110 a, which is substantially horizontal. One axial end of the first elongate tubular member 110 a connects to an inlet to the LCM test cell 108. The other axial end of the first elongate tubular member 110 a can be capped. Alternatively, one of the second, third or fourth elongate members (for example, the second elongate tubular member 110b) can connect to the other axial end instead of to the circumferential surface of the first elongate tubular member 110 a.

The second base member 116 can also include an opening through which the LCM test cell 108 is passed. The LCM test cell 108 can be vertically positioned in the opening in the second base member 116 such that an outlet to the LCM test cell 108 faces downward (that is, towards the floor 118). The inlet to the LCM test cell 108 can be formed on a circumferential surface of the LCM test cell 108. Alternatively, the inlet can be formed on an axial end surface of the LCM test cell 108, the inlet facing vertically upward (that is, away from the floor 118). In such implementations, the first elongate tubular member 110a can include a vertical section that connects the substantially horizontal section of the member 110a to the upward-facing inlet of the LCM test cell 108.

The arrangement of the reservoirs and the test cell, and the elongate tubular members, as described earlier, can enable flowing components from the reservoirs, in a sequence, to the test cell such that the LCM to be tested is formed within the LCM test cell 108. The arrangement also enables flowing an acid to the LCM test cell 108 from one of the reservoirs (or from a different reservoir (not shown)) to determine if the LCM in the LCM test cell 108 can be dissolved. The arrangement additionally enables determining the effect of the spacer fluid on the LCM test and to pump contaminants into the LCM test cell 108 to study the tolerance of the LCM to contaminants.

The disk member 200 can be coupled to the LCM test cell 108, for example, inserted into the LCM test cell 108 from the bottom, and fastened. In this manner, the region of the LCM test cell 108 between the inlet and the outlet form a fluid flow path. Because the disk member 200 is positioned within the flow path, at least a portion of the LCM test material flowed into the LCM test cell 108 flows from the inlet through the multiple openings in the disk member 200 towards the outlet. The fluid transfer network includes a fifth elongate tubular member 110e attached to the outlet of the LCM test cell 108, and a fifth valve 112 e in a flow path through the fifth elongate tubular member 110 d. The portion of the LCM test material that flows through the multiple openings in the disk member 200 and out of the outlet of the LCM test cell 108 can flow through the fifth elongate tubular member 110 e and can be collected by opening the fifth valve 112 e.

Figure 3A:
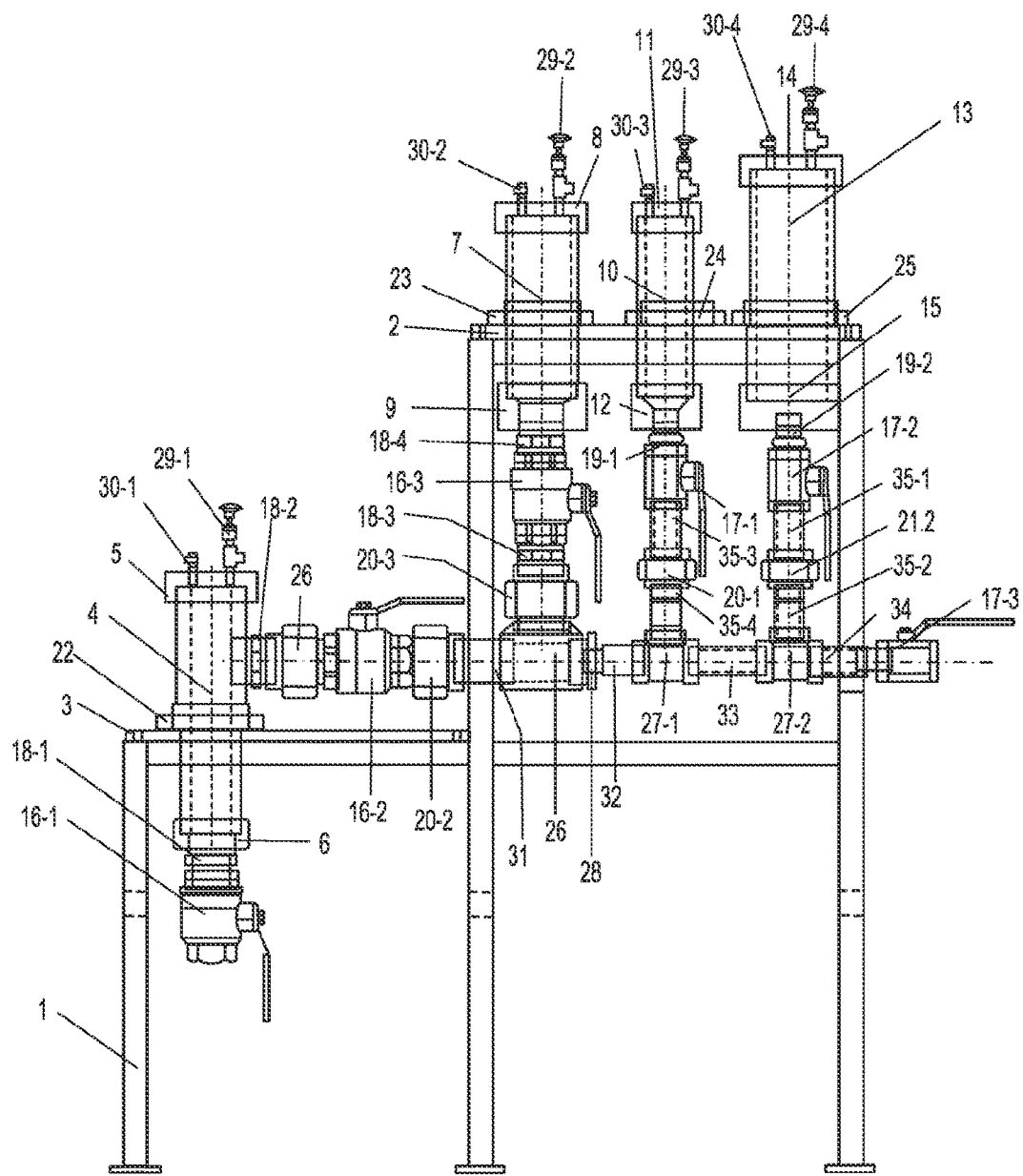
FIG. 3A is a schematic diagram of another example LCM test apparatus.
Figure 3B:
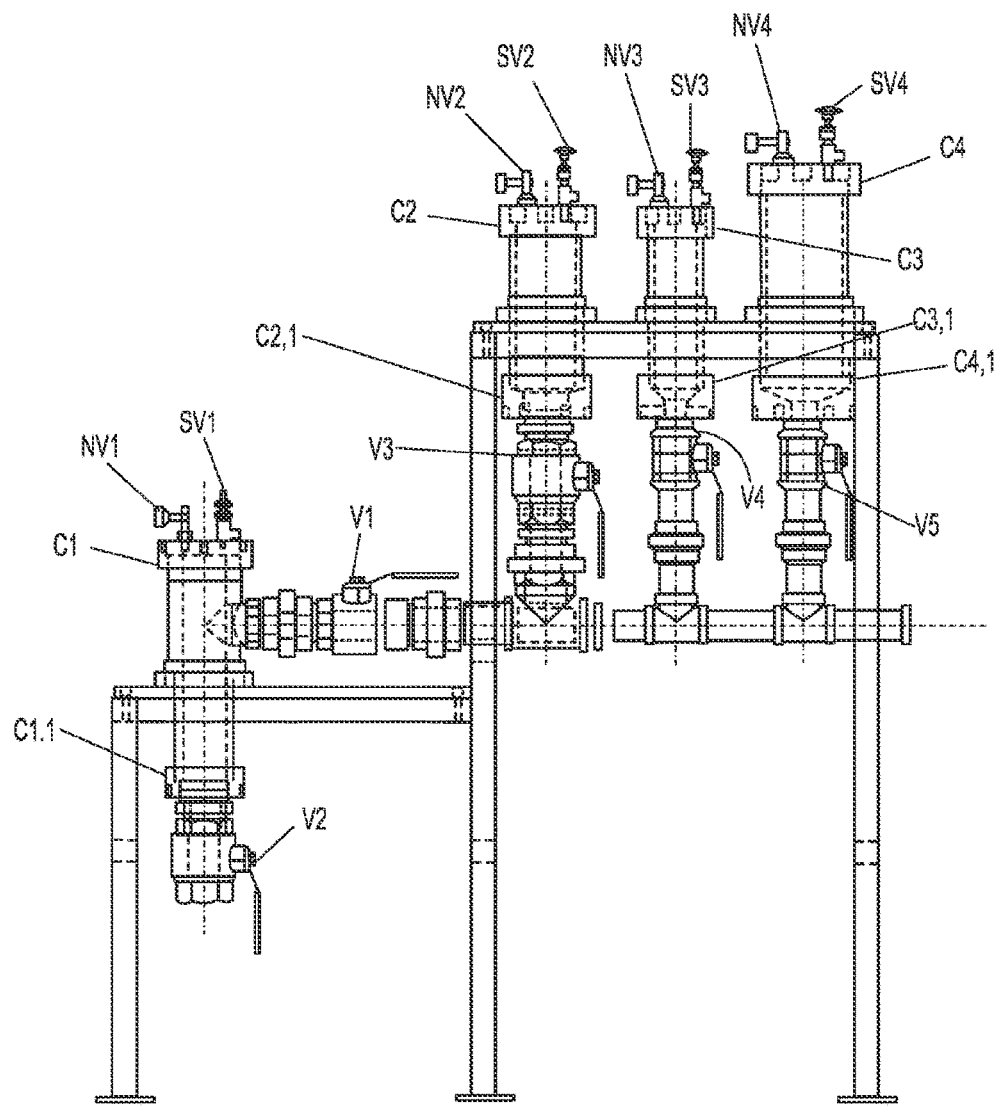
FIG. 3B is a schematic diagram of the example LCM test apparatus of FIG. 3A.

FIG. 3A is a schematic diagram of another example LCM test apparatus 300. FIG. 3B is a schematic diagram of the example LCM test apparatus 300 of FIG. 3A. In particular, FIG. 3B identifies the caps, needle valves and safety valves included in the valve network of the LCM test apparatus 300. The LCM test apparatus 300 is substantially similar to the LCM test apparatus 100 described earlier. Components of the LCM test apparatus 300 are shown in Table 1.

TABLE 1

List of Parts

| # | Description | Quantity |
|---|---|---|
| 1 | Stand | 1 |
| 2 | Locating Plate 1 Top | 1 |
| 3 | Locating Plate 2 Middle | 1 |
| 4 | Main Test Cell 2 Liter | 1 |
| 5 | Main Test Top Cap | 1 |
| 6 | Main Test Bottom Cap | 1 |
| 7 | LCM Reservoir | 1 |
| 8 | LCM Top Cap | 1 |
| 9 | LCM Bottom Cap | 1 |
| 10 | Spacer Reservoir | 1 |
| 11 | Spacer Reservoir Top Cap | 1 |
| 12 | Spacer Reservoir Bottom Cap | 1 |
| 13 | Mud Reservoir | 1 |
| 14 | Mud Reservoir Top Cap | 1 |
| 15 | Mud Reservoir Bottom Cap | 1 |
| 16 | Ball Valve 1 | 3 |
| 17 | Ball Valve 2 | 3 |
| 18 | Nipple 1 | 4 |
| 19 | Nipple 2 | 2 |
| 20 | Union 1 | 3 |
| 21 | Union 2 | 2 |
| 22 | Main Test Cell adjusting Nut | 2 |
| 23 | LCM Reservoir Cell adjusting Nut | 2 |
| 24 | Spacer Reservoir Cell adjusting Nut | 2 |
| 25 | Drilling Mud Reservoir Cell adjusting Nut | 2 |
| 26 | Tee 1 | 1 |
| 27 | Tee 2 | 2 |
| 28 | Reducer Connector | 1 |
| 29 | Safety Valve | 4 |
| 30 | Needle Valve | 4 |
| 31 | Union to Tee Connecting Pipe | 1 |
| 32 | Reducer Connector to Tee Connecting Pipe | 1 |
| 33 | Tee to Tee Connecting Pipe | 1 |
| 34 | Tee Ball Valve 2 Connecting Pipe | 1 |
| 35 | Ball Valve to Union Connecting Pipe | 4 |
| 36 | Allen Bolt | 8 (not labeled) |

The LCM is evaluated in main test cell 4 using various slotted and vugular metal disks (not shown in FIGS. 3A and 3B). For example, a sealing efficiency of the LCM is evaluated. The sealing efficiency is an ability of the LCM to prevent flow of a wellbore drilling fluid known as drilling mud through the multiple slots in the disks. A spacer fluid is sometimes used to prevent drilling mud-LCM contamination at the interface. Plugging and sealing efficiency are used to represent the same parameter. The main test cell 4 has threaded type top cap C1 and bottom cap C1.1. Pressure inlet/outlet needle valve NV1 and safe valve SV1 are fixed on the top cap C1. Ball valve V2 is attached with the bottom cap C1.1, which is the outlet of the main test cell 4. The LCM test apparatus 300 includes three reservoirs, namely, the LCM reservoir 7, the spacer fluid reservoir 10 and the mud reservoir 13. These reservoirs have respective threaded top caps (C2, C3 and C4), and bottom caps (C2.1, C3.1 and C4.1). The top caps of the reservoir chambers are fixed with respective pressure inlet/outlet needle valves (NV2, NV3 and NV4) and safe valves (SV2, SV3 and SV4). The bottom cap of the reservoir chambers are fixed with respective ball valves (V3, V4 and V5), which are connected to union. The other end of the unions of the three reservoirs are connected to Tee joints, which connect a pipe to main test cell 4 through a ball valve V1. A valve is fixed on the other end of the pipe. The entire assembly is supported by a stand (for example, a metal stand) and can be mounted on the floor. The main test cell 1 and the three reservoir chambers are interconnected through various ball valves and can be disconnected by removing the unions connecting the different parts. The ability to interconnect and disconnect the different components facilitates cleaning the test apparatus.

In operation, nitrogen is flowed into each pressure inlet needle valve (NV1, NV2, NV3 and NV4) to flow the fluids from the reservoirs into the main test cell 4. The nitrogen applies a downward pressure on the fluid forcing the fluid toward the slotted disk. An ideal LCM will not permit any fluid to flow through the slots in the disk. In practice, a discharge of less than or equal to substantially 30 milliliters (ml) (give or take about 5 ml) indicates an acceptable sealing efficiency for the LCM. In some instances, a reduction of 20-25% in the loss of the drilling fluid also indicates an acceptable sealing efficiency for the LCM. In some implementations, the nitrogen pressure can be applied to the pressure inlet needle valve of the main test cell 14 (NV4) after the fluids from the other reservoirs have been flowed into the cell 4.

Figure 4:
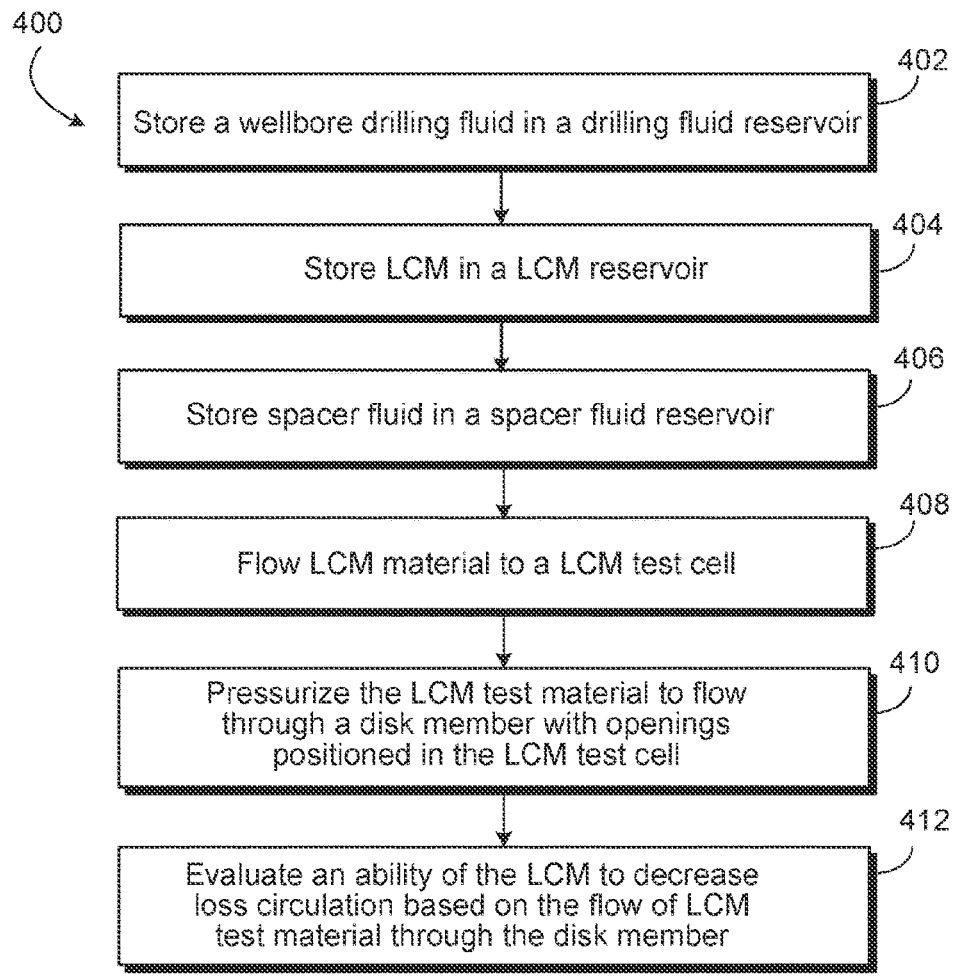
FIG. 4 is a flowchart of an example of a process for evaluating LCM using the example LCM test apparatus of FIGS. 3A and 3B.

FIG. 4 is a flowchart of an example of a process 400 for evaluating LCM using the example LCM test apparatus 300. The process can be performed by an operator of the LCM test apparatus. The process can be performed in a laboratory or under laboratory conditions. Before starting a test, all valves can be closed and all regulators can be rotated fully. All seals (for example, O-rings or similar seals) can be checked and replaced if necessary. A thin coat of grease (for example, silicone grease) can be applied around the seals and the cell caps. O-ring recesses can be checked for cleanliness and an O-ring can be inserted inside the cell recess on an axial end of the LCM test cell. A disk member with multiple openings can be selected and inserted into the LCM test cell, for example, from the bottom. As described earlier, the disk member with the multiple openings can be selected based on the loss circulation zone to be simulated using the LCM test cell. For example, to simulate a severe loss zone, a disk member in which the multiple openings have a dimension of at least 40 mm (for example, 50 mm) can be selected. To simulate moderate or seepage type loss circulation zones, a disk member with comparatively smaller openings can be selected. The bottom cap of the LCM test cell can then be fastened to the disk member. The top cap of the LCM test cell can then be fastened to the test cell body. Similarly, the respective caps of the drilling fluid reservoir, the LCM reservoir and the spacer fluid reservoir can be fastened to the respective reservoirs.

Subsequently, pre-setup for the pressure safety valve for each reservoir can be started individually. To do so, all caps and valve connected to the reservoirs can be completely closed. The spring that covers the desired set pressure can be selected, installed and adjusted to the maximum. For example, a first spring can be selected for a pressure range of 350 psi to 750 psi. A second spring can be selected for a pressure range of 1500 psi to 2250 psi. Pressure can be applied to the chamber until the required pressure is reached. The inlet valve can be closed. The safety valve can be opened until the pressure inside the chamber is released. The position of the safety valve cap can be locked.

At 402, LCM can be stored in (for example, poured into) a LCM reservoir. The LCM reservoir can be sealed using the corresponding top and bottom caps. To do so, cap C2 can be opened and the LCM placed inside the fluid-carrying volume in the LCM reservoir. Cap C2 can then be closed. At 404, a wellbore drilling fluid can be stored in (for example, poured into) a drilling fluid reservoir. At 406, spacer fluid can be stored in a spacer fluid reservoir. The respective fluids can be stored in the respective reservoirs by implementing techniques similar to step 402.

At 408, LCM can be flowed to the LCM test cell. In some implementations, a quantity of each of the LCM, the drilling fluid or the spacer fluid can be metered. In addition, the fluids can be flowed to the LCM test cell in a desired sequence, for example, LCM, spacer fluid, drilling fluid, or similar sequence. To flow the LCM to the LCM test cell, pressure can be applied for a duration (for example, two minutes or different duration) through NV2. After the duration and if sufficient LCM has been flowed to the LCM test cell, the application of pressure can be stopped and the cap C1 and the valves V1 and V3 can be closed. Similar procedure can be adopted to flow the drilling fluid or the spacer fluid (or both) using the respective caps and valves.

At 410, the LCM test material, which includes the LCM and either the drilling fluid or the spacer fluid or both, can be pressurized to flow through the disk member positioned in the LCM test cell. To do so, for example, valve V2 can be opened and a collection vessel can be positioned at the outlet of the LCM test cell. Pressure can be applied in increments (for example, in 50 psi or greater or smaller increments) until a desired test pressure is reached. The valve NV1 can be closed and the pressure in the LCM test cell left undisturbed for a duration (for example, 30 minutes or greater or smaller duration). If rapid discharge of LCM test material in bulk volume is observed through the outlet of the LCM test cell, the application of pressure can be ceased. Otherwise, the quantity of the LCM test material discharged through the outlet can be collected and recorded.

At 412, an ability of the LCM to decrease loss circulation can be evaluated based on the flow of LCM test material through the disk member. The LCM that permits no fluid discharge or the least fluid discharge through the outlet of the LCM cell is the most effective LCM. Different LCM samples can be prepared by varying (for example, increasing) the concentration of the LCM in the drilling fluid or the combination of the drilling fluid and the spacer fluid. Each LCM sample can be evaluated at different pressures applied to the LCM test cell. Each LCM sample can additionally be evaluated using different slotted disks, each having openings of different sizes. In experiments in which the LCM is made from two components, the concentration of the activator that is used to form the LCM can be varied.

After the test, all the pressure lines from needle valves NV1, NV2, NV3 and NV4 are disconnected. The pressure inside the cells is released by opening needle valves NV1, NV2, NV3 and NV4. In case of trapped pressure inside the LCM test cell, pressure is first relieved through needle valve NV1. If insufficient pressure is relieved, safety valve SV1 is used for reducing the pressure. To further release the pressure, the union for valve V1 is released slowly so that the trapped pressure can escape from the main test cell. Prior to the next test, the test cells, cell caps and all fittings can be cleaned thoroughly. All threads can be cleaned and any debris removed. All fittings can be further cleaned, for example, by blowing air. All O-rings can be lubricated to ensure proper fit and increased life. The threads can be periodically inspected for damage or wear, and replaced as necessary.

By implementing the techniques described here, the effectiveness of LCM in loss circulation zones having aperture sizes greater than 40 mm (for example, up to 50 mm) can be determined. Thus, particular implementations of the subject matter have been described. Other implementations are within the scope of the following claims.

Unless defined otherwise, all technical and scientific terms used have the same meaning as commonly understood by one of ordinary skill in the art to which these systems, apparatuses, methods, processes and compositions belong.

The singular forms "a," "an," and "the" include plural referents, unless the context clearly dictates otherwise.

As used here and in the appended claims, the words "comprise," "has," and "include" and all grammatical variations thereof are each intended to have an open, non-limiting meaning that does not exclude additional elements or steps.

"Optionally" means that the subsequently described event or circumstances may or may not occur. The description includes instances where the event or circumstance occurs and instances where it does not occur.

When the word "approximately", "about", or "similar" are used, this term may mean that there can be a variance in value of up to ±10%, of up to 5%, of up to 2%, of up to 1%, of up to 0.5%, of up to 0.1%, or up to 0.01%.

Ranges may be expressed as from about one particular value to about another particular value, inclusive. When such a range is expressed, it is to be understood that another embodiment is from the one particular value to the other particular value, along with all particular values and combinations thereof within the range.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed is:

1. A loss circulation material (LCM) testing apparatus, comprising:
   A LCM testing cell, comprising:
      an inlet for introducing a LCM testing fluid into the LCM test cell, where the LCM testing fluid comprises a slurry of LCM material and a wellbore drilling fluid;
      an outlet for passing the LCM testing fluid from the LCM test cell, where a fluid flow pathway is defined through the LCM testing cell between the inlet and the outlet;
      a disk member that is removable and that is positioned in the fluid flow pathway such that fluid flowing from the inlet to the outlet traverses through a plurality of flow openings in the disk member, where the disk member comprises a disk base and a plurality of downstream-directed extensions, and where the disk base and the plurality of downstream-directed extensions define the plurality of flow openings.

2. The apparatus of claim 1, wherein the LCM test cell is configured to be pressurized upstream of the disk member to a pressure in a range of from about atmospheric pressure to about 2000 pounds per square inch (psi).

3. The apparatus of claim 1, where the disk member is configured for a pressure differential between the upstream side and the downstream side of the disk member in a range of from about 0 to about 2000 pounds per square inch differential (psid).

4. The apparatus of claim 1, where for the disk member each of the plurality of flow openings has a flow length in a range of from about 3 mm (millimeters) to about 70 mm.

5. The apparatus of claim 1, where for the disk member each of the plurality of flow openings has an upstream entry dimension in a range of from about 5 mm (millimeters) to about 20 mm.

6. The apparatus of claim 1, where for the plurality of flow openings there is at least a first flow opening and a second flow opening, and where the first flow opening has a first upstream entry configuration in the disk base that is different than a second upstream entry configuration for the second flow opening.

7. The apparatus of claim 1, where for the plurality of flow openings there is at least a first flow opening and a second flow opening, and where the first flow opening has a first downstream exit configuration in a first downstream-directed extension that is different than a second downstream exit configuration for a second downstream-directed extension for the second flow opening.

8. The apparatus of claim 1, where for the plurality of flow openings there is at least a first flow opening having a first upstream entry configuration in the disk member and a first downstream exit configuration in a first downstream-directed extension, and where the first upstream entry configuration and the first downstream exit configuration are different.

9. The apparatus of claim 1, where for the plurality of flow openings there are an associated plurality of upstream entries, where the plurality of upstream entries are irregularly distributed on an upstream-facing side of the disk base.

10. The apparatus of claim 1, where for the plurality of flow openings there is at least a first flow opening and a second flow opening, and where the first flow opening has a different configuration than the second flow opening.

11. The apparatus of claim 1, where for the plurality of flow openings there is at least a first flow opening, and where the first flow opening has a first upstream entry configuration in the disk base that is not complimentary in shape to the configuration of the first flow opening.

12. The apparatus of claim 1, where for the plurality of flow openings there is at least a first flow opening and a second flow opening, and where the first flow opening has an associated first upstream entry with a first dimension and the second flow opening has an associated second upstream entry with a second dimension, where the first dimension and the second dimension are not the same or similar.

13. The apparatus of claim 1, where at least a portion of the disk member is made of a polymer.

14. The apparatus of claim 1, where the disk member is fabricated of a material that is chemically resistant to any corrosive effects of the LCM test fluid.

15. The apparatus of claim 1, where at least a portion of the disk member is non-opaque.

16. The apparatus of claim 1, where for the plurality of flow openings there is at least a first flow opening and a second flow opening, and where for the first flow opening has a first flow length that is different than a second flow length for the second flow opening.

17. The apparatus of claim 16, where the at least a portion of the disk member is at least one downstream-directed extension.

18. A method of evaluating a loss circulation material (LCM) comprising:
- introducing an LCM testing fluid into a LCM testing cell such that the LCM testing fluid traverses through a disk member, where the disk member has a plurality of flow openings, the plurality of flow openings defined in part by a plurality of downstream-directed extensions and where the LCM testing fluid comprises a slurry of LCM material and a wellbore drilling fluid; and
- detecting an amount of LCM testing fluid traversing the LCM test cell.

19. The method of claim 18 further comprising determining a sealing efficiency of the LCM.

20. The method of claim 18 where the LCM testing fluid further comprises a spacer fluid.

21. The method of claim 18, where detecting an amount of LCM testing fluid traversing the LCM test cell comprises visually monitoring the LCM interacting with the disk member, where at least a portion of the disk member is non-opaque.

22. The method of claim 18 further comprising applying a pressure to the LCM testing fluid upstream of the disk member.

23. The method of claim 22, where the pressure is maintained upstream of the disk member in a range of from about greater than atmospheric pressure to about 2000 psi.

24. The method of claim 22, where a pressure differential between the portion of the LCM testing cell upstream of the disk member and downstream of the disk member is maintained in a range of from about 0 to about 2000 psid.

* * * * *